United States Patent [19]
Sharp et al.

[11] Patent Number: 6,150,515
[45] Date of Patent: Nov. 21, 2000

[54] TAT-SF: COFACTOR FOR STIMULATION OF TRANSCRIPTIONAL ELONGATION BY HIV-1 TAT

[75] Inventors: Phillip A. Sharp, Newton, Mass.; Qiang Zhou, Berkeley, Calif.

[73] Assignee: Massachusetts Institute of Technology, Cambridge, Mass.

[21] Appl. No.: 09/214,564
[22] PCT Filed: Jul. 3, 1997
[86] PCT No.: PCT/US97/11713
§ 371 Date: Aug. 18, 1999
§ 102(e) Date: Aug. 18, 1999
[87] PCT Pub. No.: WO98/00695
PCT Pub. Date: Jan. 8, 1998

Related U.S. Application Data

[60] Provisional application No. 60/021,218, Jul. 3, 1996, and provisional application No. 60/033,152, Dec. 13, 1996.
[51] Int. Cl.[7] .............................. C12N 15/12; C12N 5/10
[52] U.S. Cl. ................ 536/23.5; 536/24.31; 536/24.33; 435/325; 435/252.3
[58] Field of Search .......................... 435/252.3, 6, 91.1, 435/325, 375; 536/23.1, 23.2, 24.31, 24.3, 24.33, 23.5

[56] References Cited

PUBLICATIONS

Zhou and Sharp, *The EMBO Journal*, 14(2): 321–328 (1995).
Zhou and Sharp, *Science*, 274: 605–610 (1996).
Desai et al., *Proc Natl Acad Sci USA*, 88: 8875–8879 (1991).

*Primary Examiner*—Robert A. Schwartzman
*Assistant Examiner*—Karen A Lacourciere
*Attorney, Agent, or Firm*—Wolf, Greenfield & Sacks, P.C.

[57] ABSTRACT

The invention pertains to a novel transcriptional activity factor, Tat-Stimulatory Factor, as well as genes encoding this factor and fragments and biologically functional variants thereof. The Tat-Stimulatory Factor is involved in the regulation of transcriptional elongation of HIV-1 by Tat. The invention also pertains to therapeutics involving the foregoing proteins and genes, and agents that bind to the foregoing proteins and genes. The invention also relates to methods of screening for a compound which binds to Tat-SF1, Tat-SF1-associated kinase and/or a complex of Tat-SF1 and Tat-SF1-associated kinase, as well as methods of screening for compounds which modulate Tat-SF1-mediated transcriptional activation,

13 Claims, 9 Drawing Sheets

```
    1  RNP-2 RNP-1  RNP-2 RNP-1  420              754
  N [    RRM      RRM          ░░░░░░░░░░░░░░░ ] C
     RNA RECOGNITION MOTIFS         ACID DOMAIN
     HOMOLOGY TO EWS AND FUS/TLS  CONSENSUS CASEIN KINASE II
                                   PHOSPHORYLATION SITES
```

| | |
|---|---|
| MSGTNLDGNDEFDEQLRMQELYGDGKDGDTQTDAGGEPDSLGQQPTDTPY | 50 |
| EWDLDKKAWFPKITEDFIATYQANYGFSNDGASSSTANVEDVHARTAEEP | 100 |
| PQEKAPEPTDARKKGEKRKAESGWFHVEEDRNTNVYVSGLPPDITVDEFI | 150 |
| QLMSKFGIIMRDPQTEEFKVKLYKDNQGNLKGDGLCCYLKRESVELALKL | 200 |
| LDEDEIRGYKLHVEVAKFQLKGEYDASKKKKKCKDYKKKLSMQQKQLDWR | 250 |
| PERRAGPSRMRHERVVIIKNMFHPMDFEDDPLVLNEIREDLRVECSKFGQ | 300 |
| IRKLLLFDRHPDGVASVSFRDPEEADYCIQTLDGRWFGGRQITAQAWDGT | 350 |
| TDYQVEETSREREERLRGWEAFLNAPEANRGLSVQILSLLRKAGPSRSRH | 400 |
| FSEHPSTSKMNAQETATGMAFEEPIDEKKFEKTEDGGEFEEGASENNAKE | 450 |
| SSPEKEAEEGCPEKESEEGCPKRGFEGSCSQKESEEGNPVRGSEEDSPKK | 500 |
| ESKKKTLKNDCEENGLAKESEDDLNKESEEEVGPTKESEEDDSEKESDED | 550 |
| CSEKQSEDGSEREFEENGLEKDLDEEGSEKELHENVLDKELEENDSENSE | 600 |
| FEDDGSEKVLDEEGSEREFDEDSDEKEEEEDTYEKVFDDESDEKEDEEYA | 650 |
| DEKGLEAADKKAEEGDADEKLFEESDDKEDEDADGKEVEDADEKLFEDDD | 700 |
| SNEKLFDEEEDSSEKLFDDSDERGTLGGFGSVEEGPLSTGSSFILSSDDD | 750 |
| DDDI | |

Fig. 5A

```
     1  RNP-2 RNP-1 RNP-2 RNP-1  420              754
  N [====RRM======RRM==========================] C
        RNA RECOGNITION MOTIFS         ACID DOMAIN
    HOMOLOGY TO EWS AND FUS/TLS  CONSENSUS CASEIN KINASE II
                                   PHOSPHORYLATION SITES
```

| Sequence | Pos |
|---|---|
| MSGTNLDGNDEFDEQLRMQELYGDGKDGDTQTDAGGEPDSLGQQPTDTPY | 50 |
| EWDLDKKAWFPKITEDFIATYQANYGFSNDGASSSTANVEDVHARTAEEP | 100 |
| PQEKAPEPTDARKKGEKRKAESGWFHVEEDRNTNVYVSGLPPDITVDEFI | 150 |
| QLMSKFGIIMRDPQTEEFKVKLYKDNQGNLKGDGLCCYLKRESVELALKL | 200 |
| LDEDEIRGYKLHVEVAKFQLKGEYDASKKKKKCKDYKKKLSMQQKQLDWR | 250 |
| PERRAGPSRMRHERVVIIKNMFHPMDFEDDPLVLNEIREDLRVECSKFGQ | 300 |
| IRKLLLFDRHPDGVASVSFRDPEEADYCIQTLDGRWFGGRQITAQAWDGT | 350 |
| TDYQVEETSREREERLRGWEAFLNAPEANRGLSVQILSLLRKAGPSRSRH | 400 |
| FSEHPSTSKMNAQETATGMAFEEPIDEKKFEKTEDGGEFEEGASENNAKE | 450 |
| SSPEKEAEEGCPEKESEEGCPKRGFEGSCSQKESEEGNPVRGSEEDSPKK | 500 |
| ESKKKTLKNDCEENGLAKESEDDLNKESEEEVGPTKESEEDDSEKESDED | 550 |
| CSEKQSEDGSEREFEENGLEKDLDEEGSEKELHENVLDKELEEENDSENSE | 600 |
| FEDDGSEKVLDEEGSEREFDEDSDEKEEEEDTYEKVFDDESDEKEDEEYA | 650 |
| DEKGLEAADKKAEEGDADEKLFEESDDKEDEDADGKEVEDADEKLFEDDD | 700 |
| SNEKLFDEEEDSSEKLFDDSDERGTLGGFGSVEEGPLSTGSSFILSSDDD | 750 |
| DDDI | |

Fig. 5B

```
Tat-SF1:  30  TQTDAGGEPDSLGQQ  44
              .|  .  |.| ||||
EWS:     209  SQQNTYGQPSSYGQQ  223

Tat-SF1:  82  ASSSTANVEDVHARTAEEPPQEKAPEPTDARKKGEKRKAES  122
              |.|  . .      ..|  |||| |  |  ..|
EWS:     113  AAQSAYGTQPAYPAYGQQPAATAPTRPQDGNKPTETSQPQS  153

Tat-SF1: 128  EEDRNTNVYVSGLPPDITVDEFIQLMSKFGIIMRDPQTEEFKVKLYKDNQ  177
              |.  |.  .||| ||   .|.|.   . |..  . |. .  .  . ||.
EWS:     356  EDSDNSAIYVQGLNDSVTLDDLADFFKQCGVVKMNKRTGQPMIHIYLDKET  406

Tat-SF1: 178  GNLKGDGLCCYLKRESVELALKLLDEDEIRGYKLHVEVAK  217
              | |||  |     ..|..  |  ..||  .|.
EWS:     407  GKPKGDATVSYEDPPTAKAAVEWFDGKDFQGSKLKVSLAR  446

Tat-SF1: 311  PDGVASVSFRDPEEADYCIQTLDGRWFGGRQI  342
              | | |.||   ..  ||  | |.   |  ..
EWS:     409  PKGDATVSYEDPPTAKAAVEWFDGKDFQGSKL  440
```

| | VECTOR | | | Tat-SF1 | | | FOLD * |
|---|---|---|---|---|---|---|---|
| Tat: | -† | + | FOLD ACT. | - | + | FOLD ACT. | ENHANCEMENT |
| EXP. 1 | 100 | 7228 | 72.3 | 31.7 | 7699 | 242.9 | 3.36 |
| EXP. 2 | 100 | 15779 | 157.8 | 17.0 | 16548 | 973.4 | 6.17 |
| EXP. 3 | 100 | 4899 | 49.0 | 35.3 | 10353 | 293.3 | 5.99 |
| TFEB-VP16: | - | + | FOLD ACT. | - | + | FOLD ACT. | |
| EXP. 1 | 100 | 30229 | 302.3 | 118 | 20782 | 176.1 | 0.58 |
| EXP. 2 | 100 | 18241 | 182.4 | 179 | 15080 | 84.2 | 0.46 |
| GAL4-VP16: | - | + | FOLD ACT. | - | + | FOLD ACT. | |
| | 100 | 132208 | 1322 | 95.0 | 129960 | 1368 | 1.03 |

TAT-SF: COFACTOR FOR STIMULATION OF TRANSCRIPTIONAL ELONGATION BY HIV-1 TAT

This Appln. claims benefit of provisional appln. 60/021,218 Jul. 3, 1996 and provisional appln. 60/033,152 Dec. 13, 1996.

GOVERNMENT SUPPORT

This work was funded in part by the National Institutes of Health under the Grant Nos. GM34277 and AI32486, and the National Cancer Institute under Center core Grant No. CA14051. The Government may retain certain rights in this invention.

BACKGROUND OF THE INVENTION

Intricate mechanisms regulate mRNA synthesis by control of initiation or elongation of transcription. An understanding of these mechanisms and the factors controlling these mechanisms would be important in designing therapeutic modalities for treating a variety of important medical conditions, including cancer and infection. For example, HIV-1 transcriptional elongation by Tat is essential for viral replication. Interruption of transcriptional elongation by Tat, therefore, would be highly desirable as a means for treating HIV-infected individuals.

Tat activation of HIV-1 transcription is mechanistically different from conventional activation of transcription by DNA sequence-specific transcription factors. First, most conventional activators affect transcription primarily through increasing the rate of initiation, although recent studies indicate that some prototype DNA sequence-specific transcription factors such as GAL4-VP16 can stimulate both initiation and elongation. In contrast, Tat predominantly stimulates the efficiency of elongation. Secondly, while most conventional activators interact with promoter or enhancer DNA, Tat interacts with the trans-acting responsive (TAR) RNA element. TAR is located at the 5' end of the nascent viral transcript and forms a stem-loop structure. The specific binding of Tat to TAR depends primarily upon the integrity of the bulge loop and immediately flanking sequences in the double-stranded RNA. Sequences in the apical loop of TAR are also important for Tat activation of transcription in vivo.

Control of transcriptional elongation thus has been recognized as an important step in gene regulation, but mechanisms regulating the efficiency of elongation, mediated by RNA polymerase II, have not been extensively studied. The necessity for strict control of elongation for proper gene regulation is further highlighted by the recent finding that an elongation factor, Elongin, is probably the functional target of the von Hippel-Lindau tumor suppressor protein.

SUMMARY OF THE INVENTION

The invention involves in one respect the identification, purification, and isolation of proteins, Tat-Stimulatory Factor protein, which are specifically required for Tat trans-activation. The invention also involves nucleic acid molecules encoding those proteins. The invention further involves the discovery and identification of kinases that bind the Tat-Stimulatory Factor proteins, which binding is believed important for TAT transcriptional elongation. The expression and biological activity of the proteins are necessary for transcriptional elongation, and alteration of the expression or biological activity of these proteins can be used to influence transcriptional activity, and thereby affect critical cellular processes.

The preferred nucleic acids of the invention are homologues and alleles of the coding region of the nucleic acid of SEQ ID NO: 1. The invention further embraces functional equivalents, variants, analogues and fragments of the foregoing nucleic acids and also embraces proteins and peptides coded for by any of the foregoing.

According to one particular aspect of the invention, an isolated nucleic acid molecule is provided. The molecule hybridizes under stringent conditions to a molecule consisting of the coding region of the nucleic acid sequence of SEQ ID NO:1 and it codes for a Tat-Stimulatory Factor protein. The invention further embraces nucleic acid molecules that differ from the foregoing isolated nucleic acid molecules in codon sequence due to the degeneracy of the genetic code. The invention also embraces complements of the foregoing nucleic acids. Preferred isolated nucleic acid molecules are those comprising the human cDNAs or genes corresponding to SEQ ID NO:1. Unique fragments of the foregoing molecules are specifically contemplated by the inventors.

The invention in another aspect involves expression vectors, and host cells transformed or transfected with such expression vectors, comprising the nucleic acid molecules described above. In one embodiment of the invention, the host cell is a hematopoietic T-cell precursor, such as a stem cell, and the nucleic acid is an antisense nucleic acid or a nucleic acid encoding a dominant negative mutant of the Tat-Stimulating Factor protein.

According to another aspect of the invention, an isolated nucleic acid molecule is provided which comprises a unique fragment of SEQ ID NO:1. In one embodiment the unique fragment is a portion of the segment of SEQ ID NO:1 consisting of SEQ ID NO:3. In another embodiment it is a portion of the segment of SEQ ID NO:1 beginning at nucleotide number 53 and ending at nucleotide number 2703, wherein the fragment is between 12 and 2650 nucleotides in length, and complements thereof. In one embodiment, the unique fragment is at least 150 and, more preferably, at least 200 nucleotides in length. In another embodiment, the unique fragment is between 12 and 32 contiguous nucleotides in length. In all embodiments the unique fragment includes consecutive nucleotides of SEQ ID NO:1 other than the nucleotides of SEQ ID NO:1 which code for SEQ ID NO:3.

According to another aspect of the invention, isolated polypeptides coded for by the isolated nucleic acid molecules described above also are provided as well as functional equivalents, variants, analogs and fragments thereof. In one embodiment, the polypeptide is a human Tat-Stimulatory Factor protein or a functionally active fragment or variant thereof. In another embodiment the polypeptide is a dominant negative mutant of a Tat-Stimulatory Factor protein.

The invention in another aspect involves a method for influencing transcription in a cell. An agent that selectively binds to an isolated nucleic acid molecule as described above or an expression product thereof is introduced within a cell, in an amount effective to alter transcription in the cell. Preferred agents are modified antisense nucleic acids and polypeptides. In one embodiment, transcriptional elongation activity altered, and in one particularly important embodiment, HIV-1 transcriptional elongation by Tat is altered. In this embodiment, the transcriptional elongation activity can be altered to treat an individual who is infected by HIV.

The invention in another aspect involves a method for isolating a kinase. A solution suspected of containing the kinase is contacted with a Tat-Stimulatory Factor protein or functional fragment thereof, and a material that binds to the Tat-Stimulatory Factor protein and that has kinase activity is identified and isolated.

The invention in a related aspect involves isolated kinases that are the binding partners of Tat-Stimulatory Factor proteins, and nucleic acids which encode such kinases, as well as functional fragments, variants and analogs of the foregoing.

The invention also provides isolated polypeptides which selectively bind a Tat-Stimulatory Factor protein, a kinase binding partner of a Tat-Stimulatory Factor protein or fragments thereof. Isolated binding polypeptides include antibodies and fragments of antibodies (e.g. Fab, $F(ab)_2$, Fd and antibody fragments which include a CDR3 region which binds selectively to a Tat-Stimulatory Factor protein or fragment thereof).

The invention also contemplates gene therapy for HIV-infected individuals, wherein stem cells of a donor are genetically engineered to include an agent that selectively binds to a nucleic acid molecule encoding a Tat-Stimulatory Factor protein or an expression product thereof, whereby said recombinant stem cells are resistant to intracellular HIV replication.

The invention involves methods of screening for compounds which bind to Tat-SF1, Tat-SF1 associated kinase, or a complex of Tat-SF1 and its associated kinase. The invention also involves methods for screening for compounds which modulate Tat-SF1-dependent transcriptional activation. Compounds identified by the methods of the invention are useful for detecting the presence of and/or modulating the activity of Tat-SF1, Tat-SF1 associated kinase, or a complex of Tat-SF1 and its associated kinase.

According to one aspect of the invention, a method of screening for a compound which binds to Tat-SF1 is provided. Tat-SF1 is contacted with the compound and the binding of the compound to Tat-SF1 is determined. The compound can be detectably labeled. In this preferred embodiment, determining the binding involves detecting the labeled compound bound to Tat-SF1. In another embodiment, determination of the binding of the compound to Tat-SF1 includes detecting a change in the biological activity of Tat-SF1. Preferably, Tat-SF1 biological activity is assayed by a Tat-SF1 mediated transcription assay, a Tat-SF1 immunoassay and/or a Tat-SF1-TAR binding assay in the presence and absence of the compound. In certain of the foregoing embodiments, the compound being screened which binds to Tat-SF1 is an oligonucleotide.

According to another aspect of the invention, a method for screening compounds which bind to Tat-SF1 associated kinase is provided. The Tat-SF1 associated kinase is contacted with the compound and the binding of the compound to the Tat-SF1 associated kinase is determined. In one embodiment, the compound is detectably labeled, and determining binding involves detecting the labeled compound bound to Tat-SF1. In another embodiment, determining the binding of the compound to the Tat-SF1 associated kinase involves detecting a change in the biological activity of the Tat-SF1 associated kinase. Preferably, the change in the biological activity of the Tat-SF1 associated kinase is determined by a Tat-SF1 mediated transcription assay, a Tat-SF1 associated kinase immunoassay, or a Tat-SF1 associated kinase substrate phosphorylation assay. In certain of the foregoing embodiments, the compound being screened which binds to the Tat-SF1 associated kinase is an oligonucleotide.

According to still another aspect of the invention, a method for screening a compound which binds to a complex of Tat-SF1 and Tat-SF1 associated kinase is provided. A complex of Tat-SF1 and Tat-SF1 associated kinase is contacted with the compound and the binding of the compound to the complex is determined. The compound can be detectably labeled, and determining binding involves detecting the labeled compound bound to Tat-SF1. In another embodiment, determining the binding involves detecting a change in the biological activity of the complex of Tat-SF1 and Tat-SF1 associated kinase. Preferably, a change in the biological activity of the complex is determined by a Tat-SF1 mediated transcription assay, an immunoassay of the complex of Tat-SF1 and Tat-SF1 associated kinase, a Tat-SF1 associated kinase substrate phosphorylation assay, or a Tat-SF1-TAR binding assay. In certain of the foregoing embodiments, the compound being screened which binds to the complex of Tat-SF1 and Tat-SF1 associated kinase is an oligonucleotide.

According to still another aspect of the invention, a method for screening compounds which modulate Tat-SF1 dependent transcriptional activation is provided. A mammalian cell which includes a gene encoding a Tat-SF1 polypeptide is provided and contacted with the compound. Tat-SF1 mediated transcriptional activation is determined as a measure of the modulation in Tat-SF1 mediated transcription caused by contact with the compound. Preferably, the mammalian cell also includes a gene encoding a TAT polypeptide. More preferably, the mammalian cell also includes an indicator gene encoding an indicator gene product operably linked to a TAR element. Still more preferably, the mammalian cell includes a gene encoding a Tat-SF1 associated kinase polypeptide. In certain embodiments, any one or more of or all of the Tat-SF1 polypeptide, the TAT polypeptide, the indicator gene product and/or the Tat-SF1 associated kinase polypeptide are encoded by transfected expression vectors.

In certain embodiments, the indicator gene encodes beta-galactosidase, alkaline phosphatase, chloramphenicol acetyl transferase, luciferase, or green fluorescent protein.

In certain preferred embodiments, the TAR element operably linked to the indicator gene is an HIV-1 LTR TAR element.

These and other objects and features of the invention are described in greater detail below.

BRIEF DESCRIPTION OF THE FIGURES

FIGS. 5A–C. A. Amino acid sequence (SEQ ID NO:2) and domain structure of Tat-SF1. B. Similarity between Tat-SF1 (amino acids 30–44, 82–122, 128–177, 178–217 and 311–342 of SEQ ID NO:2) and human EWS (amino acids 209–223, 113–153, 356–406, 407–446 and 409–440 of SEQ ID NO:4).

BRIEF DESCRIPTION OF SEQUENCES

Figure 1A:
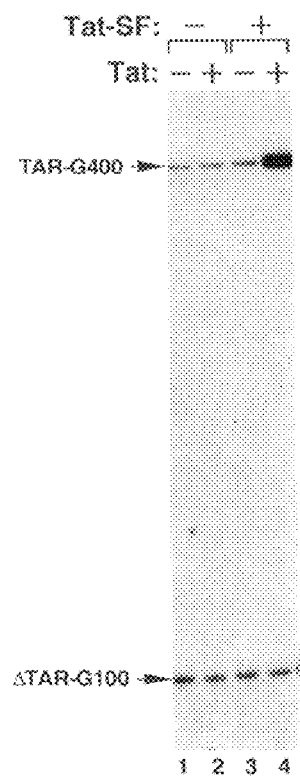
FIGS. 1A–C shows the identification of Tat-SF activity in cellular extracts. A. Tat activation of HIV transcriptional elongation requires a cellular activity, Tat-SF. B. Detection of the phosphorylated pp140 on an immobilized HIV-1 TAR RNA. C. The cysteine-rich activation domain of Tat is required for pp140 phosphorylation on TAR.

SEQ ID NO:1 is a nucleic acid including the coding region of Tat-Stimulatory Factor.

SEQ ID NO:2 is the translated amino acid sequence of the coding region of SEQ ID NO:1.

SEQ ID NO:3 is an expressed sequence tag, an amino acid sequence encoded by a portion of SEQ ID NO:1.

SEQ ID NO:4 is a portion of the amino acid sequence of EWS, which shows some homology with the amino acid of SEQ ID NO:2.

SEQ ID NO:5 is a portion of the nucleic acid of SEQ ID NO: 1.

DETAILED DESCRIPTION OF THE INVENTION

Using a reconstituted reaction that supports a TAR-dependent and Tat-specific activation of elongation, we have identified, purified, and isolated a cDNA for a novel cellular activity, Tat-Stimulatory Factor, that is specifically required for Tat trans-activation. This factor is a substrate of an associated cellular kinase. Co-transfection with the cDNA for Tat-Stimulatory Factor specifically stimulates Tat activation of HIV transcription. Sequence analysis indicates that Tat-Stimulatory Factor is related to EWS and FUS/TLS, which are members of a novel family of putative transcription factors with RNA recognition motifs and are frequently associated with many types of sarcomas. It is believed that Tat activates the processivity of elongation by recruitment of a pre-formed complex containing Tat-Stimulatory Factor and a kinase to the HIV-1 promoter through a Tat-TAR interaction.

The mRNA transcript is about 3.0 kb in length, with an open reading frame of 2271 bp. The open reading frame encodes protein of 754 amino acids with a calculated molecular weight of 85,767 Daltons. Sequence analysis of the protein reveals that it has several unique features. The protein can be roughly divided at position 420 into two halves. The COOH-terminal half is extremely rich in acidic amino acids, with 48% of the last 245 amino acid residues as glutamate or aspartate. The COOH-terminal half also contained many serine residues that are contained in a short peptide sequence matching consensus sites for phosphorylation by Casein Kinase II. Such phosphorylation would contribute more negative charges to this region. The $NH_2$ terminal half of Tat-Stimulatory Factor contains two tandem RNA recognition motifs, which have homology to many RNA-binding proteins. Further details about the protein are described in greater detail in the examples below.

It was determined that overexpression of Tat-Stimulatory Factor enhances Tat activation in vivo. Immunodepletion of the Tat-Stimulatory Factor from a partially purified fraction containing Tat-Stimulatory Factor transcriptional activity eliminates its ability to support Tat trans-activation. Thus, it is believed that Tat-Stimulatory Factor is required for Tat trans-activation.

The invention thus involves in one aspect Tat-Stimulatory Factor proteins, genes encoding those proteins, functional modifications and variants of the foregoing, useful fragments of the foregoing, as well as therapeutics relating thereto.

Homologs and alleles of the Tat-Stimulatory Factor nucleic acids of the invention can be identified by conventional techniques. Thus, an aspect of the invention is those nucleic acid sequences which code for Tat-Stimulatory Factor proteins and which hybridize to a nucleic acid molecule consisting of the coding region of SEQ ID NO:1, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent condition, as used herein, refers to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of Tat-Stimulatory Factor nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to the coding region of SEQ ID NOs:1 or 2 (FIG. 5), respectively, in some instances will share at least 50% nucleotide identity and/or at least 65% amino acid identity and in still other instances will share at least 60% nucleotide identity and/or at least 75% amino acid identity. Watson-Crick complements of the forgoing nucleic acids also are embraced by the invention.

In screening for Tat-Stimulatory Factor proteins, a Southern blot may be performed using the foregoing conditions, together with a radioactive probe. After washing the membrane to which the DNA is finally transferred, the membrane can be placed against x-ray film to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues include, but are not limited to,: CCA, CCC, CCG and CCT (proline codons); CCA, CGC, CGG, CCT, AGA and AGC (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1 or compliments of SEQ ID NO:1. A unique fragment is one that is a 'signature' for the larger nucleic acid. It, for example, is long enough to assure that its precise sequence is not found in molecules outside of the Tat-Stimulatory Factor proteins defined above. Unique fragments can be used as probes in Southern blot assays to identify such proteins, or can be used in amplification assays such as those employing PCR. As known to those skilled in the art, large probes such as 200 BP or more are preferred for certain uses such as Southern blots, while smaller fragments will be preferred for uses such as PCR. Unique fragments also can be used to produce fusion proteins for generating antibodies as demonstrated in the Examples, or for generating immunoassay components. Likewise, unique fragments can be employed to produce nonfused fragments of the Tat-Stimulatory Factor proteins, useful, for example, in immunoassays or as a competitive binding partner of the kinase which binds to the Tat-Stimulatory Factor proteins, for example, in therapeutic applications. Unique fragments further can be used as antisense molecules to inhibit the expression of Tat-Stimulatory Factor proteins, particularly for therapeutic purposes as described in greater detail below.

As will be recognized by those skilled in the art, the size of the unique fragment will depend upon its conservancy in the genetic code. Thus, some regions of SEQ ID NO:1 and its complement will require longer segments to be unique while others will require only short segments, typically between 12 and 32 BP (e.g. 12, 13, 14, 15, 16, 17, 18, 19, 20, 21, 22, 23, 24, 25, 26, 27, 28, 29, 30, 31 and 32 bases long). Virtually any segment of the region of SEQ ID NO:1 beginning at nucleotide 53 and ending at nucleotide 2703, or its complement, that is 18 or more nucleotides in length will be unique except that the unique fragments herein include consecutive nucleotides of SEQ ID NO:1 other than those nucleotides which code for SEQ ID NO:3. Those skilled in the art are well versed in methods for selecting such sequences, typically on the basis of the ability of the unique fragment to selectively distinguish the sequence of interest from non-Tat-Stimulatory Factor proteins. A comparison of the sequence of the fragment to those on known data bases typically is all that is necessary, although in vitro confirmatory hybridization and sequencing analysis may be performed.

The invention also provides isolated, functional unique fragments of SEQ ID NO:2. Such sequences are useful, for example, alone or as fusion proteins to generate antibodies, as a components of an immunoassay, as an inhibitor of Tat-Stimulatory Factor activity, as a binding partner of Tat-Stimulatory Factor binding kinases (for example, for isolating such kinases) or for inhibiting binding of such kinases to Tat-Stimulatory Factor proteins. Such unique fragments can be identified by routine assays, such as those involving testing a fragment's ability to generate antibodies if injected into a proper host, testing the fragment's ability to inhibit Tat-Stimulatory Factor activity, as described below, etc. A unique fragment of a Tat-Stimulatory Factor protein, in general, has the features and characteristics of unique fragments as discussed above in connection with nucleic acids.

As mentioned above, the invention embraces antisense oligonucleotides that selectively bind to a nucleic acid molecule encoding a Tat-Stimulatory Factor protein, to decrease transcription activity, and in particular transcriptional elongation. This is desirable in virtually any medical condition wherein a reduction in transcriptional elongation is desirable, including to reduce HIV-1 transcriptional elongation by Tat. Antisense molecules, in this manner, can be used to slow down or arrest the propagation of HIV in vivo.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457 (1994)) and at which proteins are not expected to bind. Finally, although, SEQ ID NO:1 discloses a cDNA sequence, one of ordinary skill in the art may easily derive the genomic DNA corresponding to the cDNA of SEQ ID NO:1. Thus, the present invention also provides for antisense oligonucleotides which are complementary to the genomic DNA corresponding to SEQ ID NO:1. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding Tat-Stimulatory Factor proteins or kinases that bind to Tat-Stimulatory Factor proteins, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for Tat-Stimulatory Factor proteins and fragments and variants thereof and Tat Stimulatory Factor antisense, and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as E. coli and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells. In gene therapy applications, human hematopoietic cells that are precursors of T-cells are contemplated.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase or alkaline phosphatase), and genes which visibly affect the phenotype of transformed or transfected cells, colonies or plaques. Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with the initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences, 5' or 3'. The choice and design of an appropriate vector is within the ability and discretion of one of ordinary skill in the art.

Expression vectors containing all the necessary elements for expression are commercially available and known to those skilled in the art. See Sambrook et al., *Molecular Cloning: A Laboratory Manual,* Second Edition, Cold Spring Harbor Laboratory Press, 1989. Cells are genetically engineered by the introduction into the cells of heterologous DNA (RNA) encoding the Tat-Stimulatory Factor protein or fragment or variant thereof. That heterologous DNA (RNA) is placed under operable control of transcriptional elements to permit the expression of the heterologous DNA in the host cell.

Examples of systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Another system suitable for expression in primate or canine cell lines is the pCEP4 vector (Invitrogen), which contains an Epstein Barr virus (EBV) origin of replication, facilitating the maintenance of plasmid as a multicopy extrachromosomal element.

A variety of systems for expression of proteins in bacterial, yeast, or insect cells have been described and are commercially available. Examples of such systems include the Glutathione-S-transferase (GST) Gene Fusion system available from Pharmacia Biotech, Piscataway, N.J. In this system a plasmid is constructed containing the protein sequence of interest (in this case, the transporter including the first extracellular domain) inserted in frame downstream of the 25 kDa GST domain from *S. japonicum.* Expression of the fusion protein can be induced in transfected bacterial cells and the fusion protein purified by affinity chromatography using Glutathione Sepharose 4B. Cleavage of the desired peptide from the GST sequences is achieved using a site specific protease whose recognition sequence is located immediately upstream from the cloning site. An alternative system which is desirable since it maintains eukaryotic-specific functions such as glycosylation is recombination into baculovirus. Standard protocols exist (c.f. O'Reilly et al., Baculovirus Expression Vectors: A :Laboratory Manual, IRL/Oxford University Press, 1992) and vectors, cells, and reagents are commercially available. Vaccinia virus vectors also may be employed.

The invention also permits the construction of Tat-Stimulatory Factor gene "knock-outs" in cells and in animals, providing materials for studying transcription and HIV replication.

The invention also involves polypeptides which bind to Tat-Stimulatory Factor proteins, complexes of Tat-Stimulatory Factor proteins and their kinase binding partners, and to the kinase binding partners of the Tat-Stimulatory Factor proteins. Such binding partners can be used, for example, in screening assays to detect the presence or absence of Tat-Stimulatory Factor proteins and their kinase binding partners and in purification protocols to isolate Tat-Stimulatory Factor proteins and their kinase binding partners. Such poly peptides also can be used to inhibit the native activity of the Tat-Stimulatory Factor proteins or their kinase binding partners, for example, by binding to such proteins, or their binding partners or both.

The invention, therefore, involves antibodies or fragments of antibodies having the ability to selectively bind to Tat-Stimulatory Factor proteins. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed. Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')₂ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR1 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to Tat-Stimulatory Factor proteins, their kinase binding partners and complexes of both Tat-Stimulatory Factor proteins and their kinase binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the Tat-Stimulatory Factor protein. This process can be repeated through several cycles of reselection of phage that bind to the Tat-Stimulatory Factor protein. Repeated rounds lead to enrichment of phage bearing particular sequences. DNA sequence analysis can be conducted to identify the sequences of the expressed polypeptides. The minimal linear portion of the sequence that binds to the Tat-Stimulatory Factor protein can be determined. One can repeat the procedure using a biased library containing inserts containing part or all of the minimal linear portion plus one or more additional degenerate residues upstream or downstream thereof. Yeast 2 hybrid screening methods also may be used to identify polypeptides that bind to the Tat-Stimulatory Factor proteins. Thus, the Tat-Stimulatory Factor molecule of the invention, or a fragment thereof, can be used to screen peptide libraries, including phage display libraries, to identify and select peptide binding partners of the Tat-Stimulatory Factor proteins of the invention. Such molecules can be used, as described, for screening assays, for purification protocols, for interfering directly with the functioning of Tat and for other purposes that will be apparent to those of ordinary skill in the art.

The Tat-Stimulatory Factor proteins also can be used to isolate their native binding partners, including the kinases that complex with the Tat-Stimulatory Factor proteins. Such isolation of kinases may be according to well-known methods. For example, isolated Tat-Stimulatory Factor proteins can be attached to a substrate, and then a solution suspected of containing the kinase may be applied to the substrate. If the kinase binding partner for Tat-Stimulatory Factor proteins is present in the solution, then it will bind to the substrate-bound Tat-Stimulatory Factor protein. The kinase then may be isolated. The kinase also can be isolated by successive fractionation of a solution containing the kinase, and determining whether the kinase is present with each successive phase of fractionation. Kinase activity may be determined from in vitro kinase reaction using Tat-Stimulatory Factor as the kinase substrate.

When used therapeutically, the compounds of the invention are administered in therapeutically effective amounts. In general, a therapeutically effective amount means that amount necessary to delay the onset of, inhibit the progression of, or halt altogether the particular condition being treated. Therapeutically effective amounts specifically will be those which desirably influence transcriptional activity. When it is desired to decrease such activity, then any inhibition of such activity is regarded as a therapeutically effective amount. When it is desired to increase such activity, then any enhancement of such activity is regarded as a therapeutically effective amount. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg and most preferably from about 0.2 mg//kg to about 20 mg/kg, in one or more dose administrations daily, for one or more days.

The therapeutics of the invention can be administered by any conventional route, including injection or by gradual infusion over time. The administration may, for example, be oral, intravenous, intraperitoneal, intramuscular, intracavity, intrarespiratory, subcutaneous, or transdermal.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene or fragment thereof into a cell(s) of a subject and returning the genetically engineered cell(s) to the subject. The functional copy of the gene or fragment thereof is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654.

As an illustrative example, primary human blood cells which are precursors of T-cells can be obtained from the bone marrow of a subject who is a candidate for such gene therapy. Then, such cells can be genetically engineered ex vivo with DNA (RNA) encoding an agent that binds to a Tat-Stimulatory Factor nucleic acid or expression product thereof. The genetically engineered cells then are returned to the patient. Such recombinant cells are expected to resist intracellular HIV replication.

The invention also contemplates targeting to particular cells the nucleic acids and proteins of the invention, including specifically antisense nucleic acids and agents that bind Tat-Stimulatory Factor proteins. Targeting may be tissue-specific, using targeting agents known to those of ordinary skill in the art. Methodologies for targeting include conjugates, such as those described in U.S. Pat. NO. 5,391,723 to Priest. Another example of a well-known targeting vehicle is liposomes. Liposomes are commercially available from Gibco BRL (Life Technologies, Inc., Gaithersburg, Md.). Numerous methods are published for making targeted liposomes. A preferred cell type is a T-cell, and, in particular, a T-cell infected with HIV.

According to another aspect of the invention, a method of screening for compounds which bind to Tat-SF1, Tat-SF1-associated kinase, or a complex of Tat-SF1 and Tat-SF1-associated kinase is provided.

The methods disclosed herein are useful for identifying specific compounds or molecules which bind to Tat-SF1, Tat-SF1 associated kinase or a complex of Tat-SF1 and Tat-SF1 associated kinase. Such compounds can have utility as reagents for affinity purification, for example where the compound is immobilized and used to "capture" Tat-SF1, Tat-SF1 associated kinase or the complex of Tat-SF1 and Tat-SF1 associated kinase from a biological extract such as a cell or tissue homogenate. Such compounds can also be used for localization of Tat-SF1, Tat-SF1 associated kinase or a complex of Tat-SF1 associated kinase in an intact biological system such as a cell or a tissue. The methods disclosed herein are also useful for preparation of a "library" of high probability drug candidates. Compounds can be identified as binding Tat-SF1, Tat-SF1 associated kinase or complex of Tat-SF1 associated kinase by a change in a selected biological activity, such as modulation of Tat-SF1-mediated transcriptional activity, Tat-SF1 associated kinase phosphorylation activity and the like. High probability drug candidates are those compounds which cause a change in a biological activity. Such changes in activity can provide potential therapeutic benefits. Compounds identified by in vitro assays as potential drug candidates can be tested subsequently in cell- or animal-based disease models to determine more accurately the therapeutic potential of the drug candidates.

One screening method is an in vitro binding assay of a type familiar to one of ordinary skill in the art. To preform such an assay, a test compound is contacted with the Tat-SF1, Tat-SF1-associated kinase, or a complex of Tat-SF1 and Tat-SF1-associated kinase and the binding of the compound to the Tat-SF1, Tat-SF1-associated kinase, or a complex of Tat-SF1 and Tat-SF1-associated kinase is determined. The binding can be determined in a number of ways. For example, binding of a labeled compound can be detected by methods well known to those of ordinary skill in the art. Binding of a compound also can be determined by a competitive binding assay, such as by a reduction in binding of an antibody to the Tat-SF1, Tat-SF1-associated kinase, or a complex of Tat-SF1 and Tat-SF1-associated kinase or by the inhibition of binding between Tat-SF1 and Tat-SF1 associated kinase. Binding of a compound also can be determined by a change in electrophoretic mobility or chromatographic elution profile of Tat-SF1, Tat-SF1-associated kinase, or a complex of Tat-SF1 and Tat-SF1-associated kinase relative to the profile of such a polypeptide (or complex) not bound by the compound.

Preferably, the compound is an oligonucleotide. Oligonucleotides useful in the invention can be prepared according to standard methods in the art. Oligonucleotides which bind to Tat-SF1, Tat-SF1-associated kinase, or a complex of Tat-SF1 and Tat-SF1-associated kinase are preferably prepared by binding and screening for binding activity, followed by random or targeted mutation of the nucleotides which constitute the oligonucleotide in an iterative fashion. Commercially available libraries can be screened or, as would be more likely, can be prepared for screening. Preparation of peptide libraries are described herein. Lam (*Nature* 354:82–84, 1991) also describes combinatorial methods for creating libraries of synthesized peptides on polystyrene beads, each bead carrying only one peptide. Similar procedures are known for making libraries of oligonucleotides. Methods for the selection of several classes of molecules (including oligonucleotides, peptides, and RNAs) also are described in Abelson, *Science* 249:488–489, 1990; Ellington et al., *Nature* 346:818–822, 1990; Tuerk et al., *Science* 249:505–510, 1990; Irvine et al., *J. Mol. Biol.* 222:739–761, 1991; Bock et al., *Nature* 355:564–566, 1992; Ellington et al., *Nature* 355:850–852, 1992; Gallop et al., *J. Med. Chem.* 37:1233–1251, 1994; Gordon et al., *J. Med Chem.* 37:1385–1401, 1994; and Gold, *J. Biol. Chem.* 270:13581–13584, 1995.

In one embodiment of the assay, the compound is detectably labeled. The binding of the labeled compound bound to Tat-SF1, Tat-SF 1-associated kinase, or a complex of Tat-SF1 and Tat-SF1-associated kinase then can be determined by any method known to one of skill in the art. The particular method chosen to detect the labeled compound will depend on the nature of the label. For instance, a radioactively labeled compound can be detected by scintillation counting, autoradiography, and phosphorimaging. Fluorescently labeled compounds can be detected by fluorometry. Other detectable labels are known in the art, along with suitable detection methods.

The compound also can be labeled with a molecule which serves as a binding point for a detectable label. For example, a compound can be labeled with a biotin molecule which serves as an binding point for a streptavidin molecule which is detectably labeled.

Other preferred methods for determining the binding of a compound include detecting a change in a biological activity of the Tat-SF1, Tat-SF1-associated kinase, or a complex of Tat-SF1 and Tat-SF1-associated kinase. Determinable biological activities include Tat-SF1 mediated transcription from TAR elements, changes in protein conformation and/or protein-protein interaction which are detectable in an immunoassay, e.g. by antibody binding, Tat-SF1-associated kinase substrate phosphorylation, and binding of Tat-SF1 to a TAR element. For example, Tat-SF1 mediated transcription can be determined by a reconstituted transcription assay in which Tat-SF1 is combined with transcription factors required to initiated and elongate transcription of a RNA containing a TAR element. The change in transcription mediated by Tat-SF1 which is caused by binding of a compound can be readily determined by comparing the transcription in the presence and in the absence of the compound. Tat-SF1-associated kinase substrate phosphorylation can be determined by inclusion of radiolabeled ATP in a phosphorylation reaction and determined by observing the difference in the radiolabel incorporated into a substrate of the Tat-SF1-associated kinase. Modulation of binding of Tat-SF1 to a TAR element by binding of a compound to Tat-SF1, Tat-SF1-associated kinase, or a complex of Tat-SF1 and Tat-SF1-associated kinase can be determined by a well-known assay such as an electrophoretic mobility shift assay (EMSA). A change in electrophoretic mobility observed upon contacting the compound with Tat-SF1, Tat-SF1-associated kinase, or a complex of Tat-SF1 and Tat-SF1-associated kinase will reflect a change in the binding to a TAR element. Changes in protein conformation and/or protein-protein interaction are detectable by immunoassays using antibodies which recognize a particular protein conformation or protein-protein interaction such as the interaction of Tat-SF1 and Tat-SF1-associated kinase. A change in antibody binding subsequent to contacting Tat-SF1, Tat-SF1-associated kinase and/or a complex of the two with a compound is readily determined using standard immunoassay techniques. Immunoassays which measure disruption of antibody binding to a particular epitope of Tat-SF1, Tat-SF1-associated kinase and/or a complex of the two are useful for determining binding of a compound to that particular epitope. One of ordinary skill in the art will recognize that a panel of antibodies which recognize a variety of epitopes will enable determination of the binding site of a compound which binds to Tat-SF1, Tat-SF1-associated kinase and/or a complex of the two. Biological activities and methods of determining a change in the activities subsequent to binding of a compound to Tat-SF1, Tat-SF1-associated kinase, or a complex of Tat-SF1 and Tat-SF1-associated kinase, are described more fully in the Examples below.

It is not intended that the foregoing represents an exhaustive listing of methods useful for determining the binding of a compound to Tat-SF1, Tat-SF1-associated kinase, or a complex of Tat-SF1 and Tat-SF1-associated kinase. Additional detectable labels, or biological activities of Tat-SF1, Tat-SF1-associated kinase, or a complex of Tat-SF1 and Tat-SF1-associated kinase will be apparent to one of ordinary skill in the art.

According to another aspect of the invention, a method of screening for compounds which modulate Tat-SF1-mediated transcriptional activity is provided. The method involves (1) providing a mammalian cell containing a gene encoding a Tat-SF1 polypeptide; (2) contacting the mammalian cell with one or more compounds, preferably under conditions to induce Tat-SF1 mediated transcription; and (3) determining the Tat-SF1 mediated transcriptional activation.

Cell-based screening methods are provided herein for determining the Tat-SF1-mediated transcriptional activity modulating potential of compounds. These methods are useful for identifying compounds which can modulate Tat-SF1-mediated transcriptional activity in the presence of cellular proteins and other factors involved in the transcription of genes in a cell. Thus, such methods permit screening of compounds in a variety of cells which may be particularly relevant to a disease state. For example, to identify compounds which are useful for reducing Tat-SF1-mediated transcriptional activity as a means of reducing HIV-1 infection, one of ordinary skill in the art can select an appropriate cell within the host range of HIV-1, such as a T cell, to perform the screening assay in.

The skilled artisan can readily determine the effect of a test compound on Tat-SF1-mediated transcriptional activation in a cell-based assay. It is known that the presence of Tat-SF1 in a cell stimulates transcription of genes which are operably linked to a TAR sequence, in particular by increasing elongation of nascent transcripts. Thus detection of a change in Tat-SF1 mediated-transcriptional activation involves detecting increased (or decreased) transcription of a TAR-linked nucleic acid. The skilled artisan can choose a nucleic acid sequence to link to a TAR element, operably link the TAR element to the nucleic acid using standard molecular biology techniques, and test for a change in transcription in nucleic acid by standard techniques, e.g., quantitantive nucleic acid hybridization, polymerase chain reaction amplification, nuclease protection assay and the like. Alternatively, one of ordinary skill in the art can use a nucleic acid which contains a TAR element in the foregoing assay to determine the effect of a test compound on Tat-SF1-mediated transcriptional activity. For example, HIV-1 sequences containing a TAR element can be used in such an assay, such as a reporter construct containing HIV-1 LTR linked to the bacterial CAT gene. Preferably an indicator gene is transcribed and the amount of indicator gene product is determined in the presence and the absence of the compound.

In preferred embodiments, the mammalian cell used in the assay of Tat-SF1-mediated transcriptional activation modulating activity also contains a gene encoding a Tat polypeptide and/or an indicator gene operably linked to a TAR element and/or a gene encoding a Tat-SF1-associated kinase polypeptide. These genes can be included in a variety of mammalian expression vectors, including plasmid- or virus-based episomal vectors and vectors which integrate into the host cell chromosomes, as is known to those skilled in the art. The genes described above can be introduced into the mammalian cell by standard procedures, or can be resident in the cell, such as encoded by the cell's chromosomal nucleic acid. Standard procedures for introducing nucleic acids into a mammalian cell include, but are not limited to, physical means such as transfection, electroporation and bombardment with nucleic acid-coated microparticles, and biological means such as receptor-mediated endocytosis using targeted nucleic acids or nucleic acids contained in targeted liposomes and viral infection. The particular vectors and/or means of introducing genes may depend on the mammalian cell chosen for the assay. The cells and cell lines useful in such assays include HeLa cells, COS cells and the like.

Of course, any of the foregoing genes can include only part of the gene and/or encode only a part of the polypeptide where the gene product to be detected is a nucleic acid, or where the portion of the polypeptide encoded by the gene retains the activity of the whole polypeptide or an epitope bound by an antibody. For example, an indicator gene need only encode a RNA gene product that is detectable by hybridization in an assay such as RNase protection, oligonucleotide hybridization, or reverse transcriptase polymerase chain reaction (RT-PCR). Where a polypeptide gene product is to be detected, a fragment which is sufficient to retain a detectable activity in an immunoassay, or a enzymatic activity assay, would be sufficient to meet the criteria disclosed above.

As used herein, modulation of Tat-SF1-mediated transcriptional activation refers to the ability of a compound to modulate Tat transcriptional activation, mediated by Tat-SF1, from a TAR RNA element. Thus, a Tat-SF1-mediated transcriptional activation modulating activity refers to the ability of a compound to reduce or increase the ability of Tat-SF1 to stimulate Tat-dependent transcriptional elongation of RNA molecules containing a TAR element. For example, compounds which have Tat-SF1-mediated transcriptional activation modulating activity, include compounds which disrupt the binding of Tat-SF1 to a TAR element, compounds which disrupt the binding of Tat-SF1 to a Tat-SF1-associated kinase, compounds which disrupt the phosphorylation of Tat-SF1 by a Tat-SF1-associated kinase, compound which disrupt the recruitment of additional transcription factors to the RNA containing a TAR element, and the like.

Tat and Tat-SF1 proteins can bind to a TAR element in a promoter which controls the transcription of an indicator gene. The indicator gene product, whether nucleic acid or protein, provides a readily detectable output for screening compounds for Tat-SF1-mediated transcriptional activation modulating activity. An indicator gene permits high throughput screening of a number of compounds at one time. Depending on the choice of indicator gene, and its gene product, automation of the methods disclosed herein is also contemplated.

Preferred indicator genes encode an indicator gene product which is easily detectable with or without disruption of the mammalian cell. Gene products such as RNA transcripts of the gene can be detected by hybridization assays or any other assay which detects nucleic acids of a specific sequence. Preferably, hybridization assays are conducted under stringent conditions as defined above. Indicator gene products which are proteins can be detected by any technique suitable for detection of proteins. For example, an indicator gene can encode an indicator gene product to which antibodies have been raised. Such antibodies which selectively bind to the indicator gene product can be employed in immunoassays to determine the amount of protein produced as a result of increased Tat-responsive transcription in the presence and absence of a compound. Antibodies useful in the detection of indicator gene products include commercially available antibodies such as antibodies to green fluorescent protein (Clontech, Palo Alto, Calif.), $E.$ $coli$ bacterial alkaline phosphatase, $\beta$-galactosidase (Boehringer Mannheim, Indianapolis, Ind.), and luciferase (Cortex Biochemicals, San Leandro, Calif.).

The indicator gene product can be a protein which has an enzymatic activity that can be assayed. Methods for determining the amount of such enzymes by colorimetric means (for example, conversion of X-gal into a blue product by $\beta$-galactosidase) or radioactive means (for example, addition of a $^3$H-acetyl or $^{14}$C-acetyl group to a chloramphenicol molecule by chloramphenicol acetyl transferase) will be known to one of ordinary skill in the art. Other indicator gene products, such as green fluorescent protein, are directly detectable by colorimetric means.

Preferably, the indicator gene is selected from the group consisting of the genes encoding the following proteins: $\beta$-galactosidase, alkaline phosphatase, chloramphenicol acetyl transferase, luciferase, and green fluorescent protein. However, the skilled artisan may select any indicator gene for use in accordance with the methods of the invention provided that the indicator gene product is detectable.

The indicator gene is operably linked to a promoter containing at least one TAR element which drives expression of the indicator gene by serving as the locus for binding of Tat, Tat-SF1, associated proteins and a RNA polymerase.

The nucleic acid molecules introduced into the mammalian cell may be contained on a plasmid or other extrachromosomal nucleic acid, or may be incorporated into the cell's chromosomes. Non-chromosomal nucleic acids include plasmids, phagemids, bacteriophage genomes, virus genomes, and the like. Non-chromosomal nucleic acids useful for preparation of expression vectors are well known in the art and thus are not described further here.

EXAMPLES

Example 1

Tat Activation of HIV-1 Transcription Requires A Specific Cellular Activity, Tat-SF We have previously established a partially reconstituted transcription reaction that supports a Tat-specific and TAR-dependent activation of HIV transcription (Zhou and Sharp, $EMBO$ $J.$ 14: 321–328, 1995; FIG. 1A). This reaction requires a Tat-SF (Tat-Stimulatory Factor) activity that is specific for Tat stimulation of elongation. It also requires a phosphocellulose 0.5–1.0 M KOAc fraction of HeLa nuclear extract, termed the pc-D fraction, and the purified basal factors TFIID, TFIIA, and transcription factor Sp1. Reactions containing these components, but lacking Tat-SF activity supported activation by Sp1 and GAL4-VP16 (Zhou and Sharp, 1995), but not by Tat (lanes 1 and 2, FIG. 1A). The transcription reactions were performed as follows. Reconstituted transcription reactions containing both templates pHIV+TAR-G400 and pHIVTAR-G100 were performed in the absence (−) or presence (+) of the 0.5 M KCl Q-Sepharose chromatographic fraction containing Tat-SF activity as described previously (Zhou and Sharp, 1995). The pc-D fraction and purified TFIIA, TFIID, and Sp1 were present in all reactions. G-less cassettes of two different lengths were inserted into the above two templates at position +955 downstream of the HIV-1 initiation site to measure the effect of Tat on transcriptional elongation. Transcripts derived from these two templates were digested by RNase T1 and the resulting 400- and 100-nucleotide G-less RNA fragments were separated in a denaturing polyacrylamide gel, and their positions were indicated by the arrows. In the presence of a partially purified Tat-SF fraction, Tat specifically increased the number of transcripts elongating beyond 1000 nucleotides from a HIV-1 promoter containing the wild-type TAR element (pHIV+TAR-G400), but not from an internal control promoter with a mutant TAR (pHIVTAR-G100, compare lanes 3 and 4).

The pc-D fraction was shown by Western blotting to contain the basal transcription factors TFIIB, IIE, IIF, IIH, and RNA polymerase II (Zhou and Sharp, 1995). This fraction probably also contains other activities important for Tat function, because it can not be substituted with highly purified basal transcription factors. Using the reconstituted reaction detailed above to follow the activity, Tat-SF was further purified by several chromatographic steps. HeLa nuclear extract in buffer D/0.1 M KCl (20 mM Hepes-KOH, pH 7.9/20% (vol/vol) glycerol/0.1 M KCl/0.2 mM EDTA/ 0.5 mM dithiothreitol/0.5 mM PMSF) was loaded on a phosphocellulose column preequilibrated with the same buffer. The flowthrough was loaded on a DEAE-Sepharose FF (Pharmacia, Piscataway, N.J.) matrix column preequilibrated with buffer D/0.1 M KCl. After washing the column with the same buffer, Tat-SF activity was eluted from the column with buffer D/0.3 M KCl. This fraction was dialyzed against buffer D/0.1 M KCl and applied to a Q-Sepharose FF (Pharmacia) matrix column preequilibrated with the same buffer. The column was washed with buffer D/0.1 M KCl and the bound proteins were eluted with a 0.1–0.7 M KCl gradient made in buffer D. Fractions were analyzed for Tat-SF activity in reconstituted transcription assays and for pp140 in kinase reactions (as described below). The 0.4–0.5 M KCl Q-Sepharose fraction containing Tat-SF activity and pp140 was dialyzed against buffer D/0.1 M KCl and applied to a Heparin Sepharose column. After washing the column extensively with buffer D/0.1 M KCl, Tat-SF/pp140 was eluted with increasing salt concentrations and was found mostly in 0.2–0.4 M KCl fractions. These fractions were combined, dialyzed to 0.1 M KCl, and loaded on a Glutathione Sepharose (Pharmacia) column containing GST-Tat fusion proteins. After washing with buffer D/0.4 M KCl, Tat-SF/pp140 was eluted from the column with buffer D containing 1.4 M KCl. The estimated overall purification after these steps was ~3000-fold.

Example 2

Figure 1B:
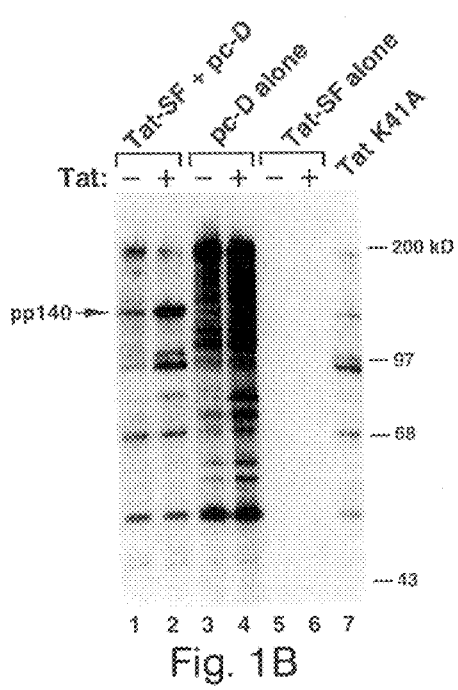

Detection of a Complex Containing Tat, a Cellular Kinase and a 140 kD Phosphoprotein in the Transcription Reaction Phosphorylation of RNA polymerase II has been implicated in regulation of the processivity of elongation (O'Brien et al., Nature 370:75–77, 1994; Dahmus, *Biochim Biophys Acta* 1261:171–182, 1995). To investigate whether protein phosphorylation might be associated with Tat-SF, an immobilized HIV TAR RNA was used to collect bound proteins from a reconstituted transcription reaction in the presence of $\gamma$-$^{32}$P ATP. Referring to FIG. 1B, biotinylated TAR RNA (nucleotides +1 to +82) immobilized on the Paramagnetic beads was introduced into the kinase reactions containing $\gamma$-$^{32}$P ATP (10 mCi) and either the pc-D fraction alone (lanes 3 and 4), or the Tat-SF fraction alone (lanes 5 and 6), or both pc-D and Tat-SF factions together (lanes 1, 2, and 7). Recombinant wild type Tat protein (13 ng) was included in the reactions shown in lanes 2, 4, and 6. Tat mutant TatK41 A (13 ng) was present in lane 7 (Rice and Carlotti, *J. Virol* 64:1864–1868, 1990). After incubation for 10 min at 30° C., the TAR RNA beads were washed extensively in buffer D containing 100 mM KCl and 0.1% NP-40 and the bound proteins were analyzed by SDS-PAGE. In reactions containing either the pc-D fraction alone (lanes 3 and 4, FIG. 1B) or the Tat-SF fraction alone (lanes 5 and 6), addition of Tat did not consistently affect the phosphorylation of proteins on immobilized TAR. When both fractions were incubated together in the presence of Tat, phosphorylation of a protein of approximately 140 kD, termed pp140, was observed (FIG. 1B, lane 2). In the absence of Tat, however, only a small amount of phosphorylated pp140 was detected (lanes 1). Thus, collection of a phosphorylated pp140 on TAR required the presence of the pc-D fraction, the Tat-SF fraction, and Tat. This suggested the existence of a complex on TAR that consists of Tat, a cellular kinase probably derived from the pc-D fraction, and the kinase substrate pp140 from the Tat-SF fraction (see below).

An intact Tat activation domain was necessary for pp140 phosphorylation on TAR. When a non-functional Tat mutant (K41A; Rice and Carlotti, 1990), which has the lysine at position 41 substituted by alanine, was present in the kinase reaction (FIG. 1B, lane 7), the amount of phosphorylated pp140 collected on the immobilized TAR was significantly reduced (compare lanes 2 and 7). Importantly, this was not due to a decreased ability of K41A to interact with TAR, since K41A bound to TAR as efficiently as wild type Tat in a gel mobility-shift assay.

Figure 1C:
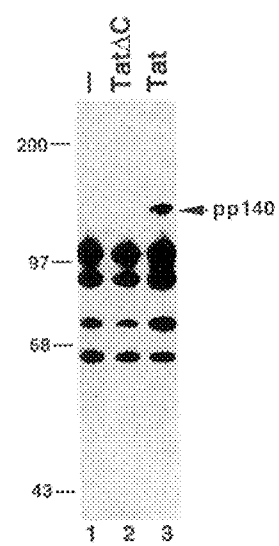

Similar results were also obtained with another Tat mutant (TatC), which lacks the cysteine-rich activation domain (amino acids 22 to 37; Rice and Carlotti, 1990) and is completely defective for transcriptional activity (FIG. 1C). Kinase reactions containing an immobilized TAR were prepared as above. Recombinant wild type Tat protein (13 ng) or Tat mutant (TatC, 13 ng) lacking the cysteine-rich domain (amino acid 22–37) was included in the reactions as indicated. No Tat was present in the control reaction (lane 1).

Figure 2A:
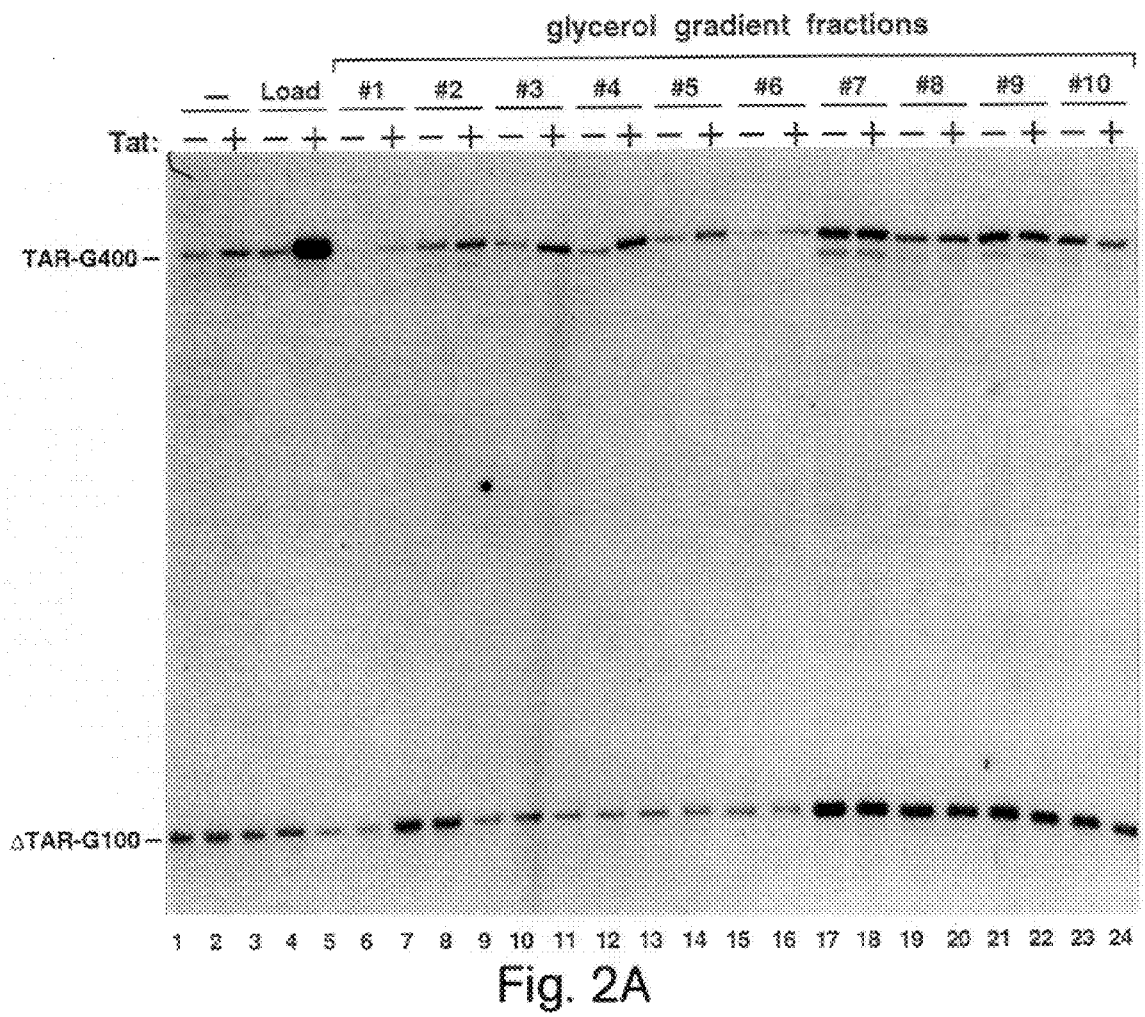
FIGS. 2A–B shows that Tat-SF transcriptional activity and pp140 co-peaked during glycerol gradient sedimentation. A. Detection by transcription reaction. B. Detection by kinase assay.
Figure 2B:
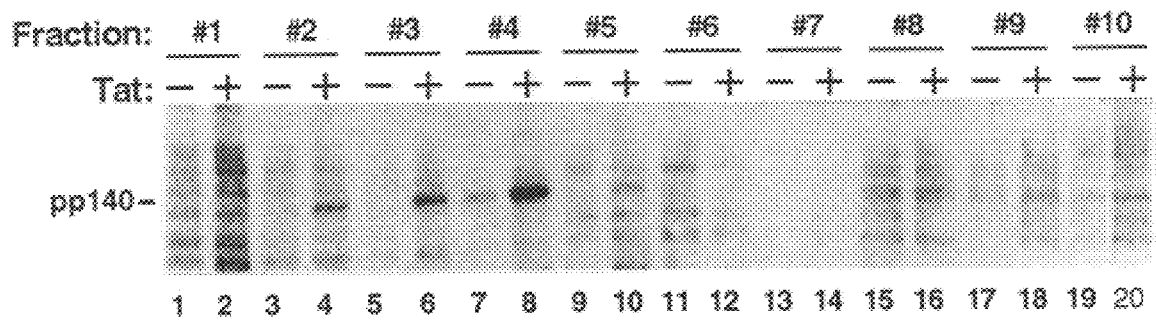

The polypeptide pp140 co-purified and co-titrated with Tat-SF transcriptional activity during purification through multiple chromatography steps. For example, when partially purified Tat-SF was sedimented through a glycerol gradient and the first 10 fractions were analyzed in the reconstituted transcription assay for the presence of Tat-SF activity (FIG. 2A), Tat-SF activity and pp140 co-peaked. A 0.2–0.4 M KCl Heparin Sepharose fraction (load, lanes 3 and 4), prepared as described above, containing Tat-SF activity was loaded onto a 12–35% glycerol gradient and subjected to ultracentrifugation. The first 10 of a total 16 fractions were tested for Tat-SF activity in the reconstituted transcription reactions in the absence (−) or presence (+) of Tat as in FIG. 1A. Control reactions (lanes 1 and 2) did not contain Tat-SF fraction. Protein molecular weight markers were sedimented in a parallel gradient and analyzed by silver staining. The peak of Tat-SF activity that supported Tat trans-activation was in fractions #4 and #3, corresponding to a native molecular mass of approximately 100 kD. When the same fractions were analyzed in the kinase assay for the presence of pp140 in a kinase assay as described in FIG. 1B (see FIG. 2B), phosphorylation of pp140 was also most evident in fractions #4 and #3, in agreement with the transcription results.

Example 3

Purification of pp140 By Tat Affinity Column Chromatography

Figure 3A:
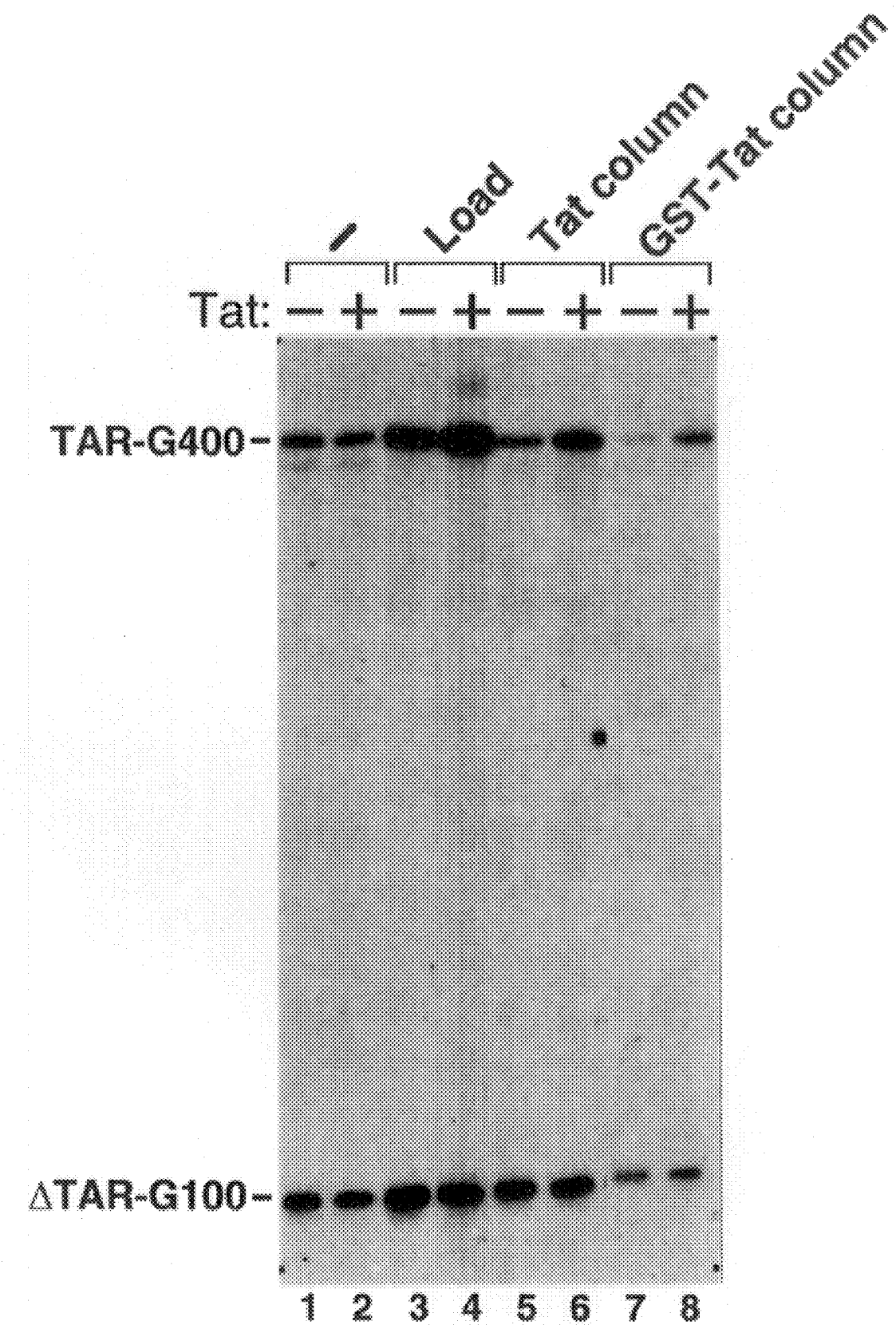
FIGS. 3A–C depicts purification of pp140 and Tat-SF transcriptional activity by Tat affinity columns. A. Eluates of the columns were tested for transcription activity. B. The same eluates were tested for the presence of pp140 in a kinase assay. C. A silver-stained SDS gel of the above two fractions is shown.
Figure 3B:
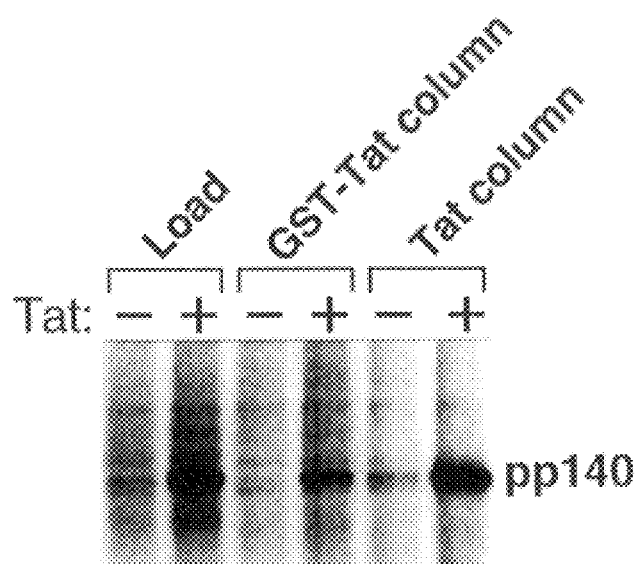
Figure 3C:
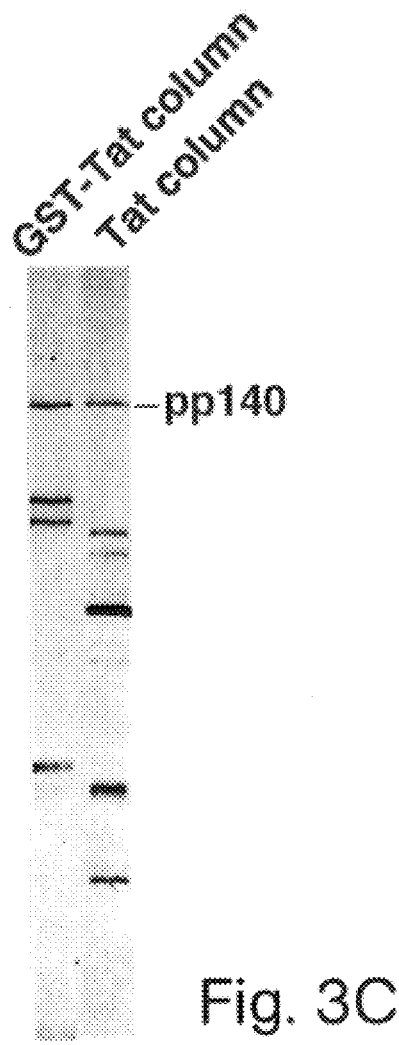

As noted above, detection of the phosphorylated pp140 on TAR requires the presence of the pc-D fraction, the Tat-SF fraction, and Tat. Sequential incubations of these components with an immobilized TAR revealed a stable and direct interaction between Tat and a cellular kinase and between Tat and pp$^{140}$. Therefore, columns containing immobilized Tat were used to affinity-purify Tat-SF/pp140. The 0.2–0.4 M KCl Heparin Sepharose fraction (load) containing Tat-SF activity described in Example 1 was subjected to fractionation through an Affi-Gel 10 matrix column (Bio-Rad, Hercules, Calif.) containing immobilized Tat. Tat-SF activity was eluted from the column with increasing salt concentrations. The 0.6 M KCl fraction was analyzed in FIG. 3. Fractions eluted from either a GST-Tat column or a Tat affinity column were analyzed in reconstituted transcription assays for the presence of Tat-SF activity (FIG. 3A). Both fractions were enriched in Tat-SF activity which supported a Tat-specific and TAR-dependent activation. The same two fractions were tested in a kinase assay as described in Example 1 and were found to contain pp140 (FIG. 3B). When analyzed by silver staining, the polypeptide profiles of these two fractions were different overall, with the only common band having a mobility of 140 kD (FIG. 3C). This polypeptide was judged to be pp140 and probably a component of Tat-SF activity.

Figure 4A:
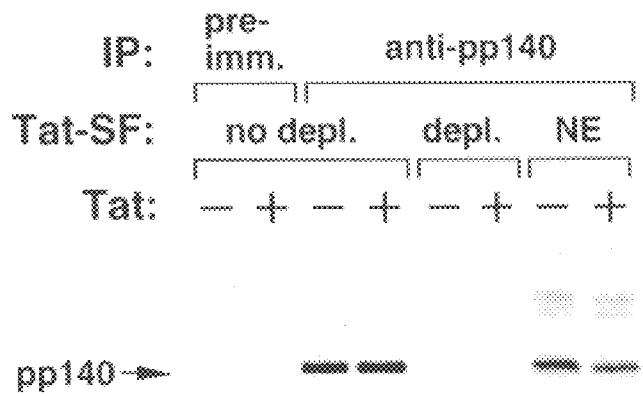
FIGS. 4A–C shows that the presence of pp140 is required for Tat-SF activity. A. pp140 and a cellular kinase form a complex independently of Tat. B. Immunodepletion of pp140 from a partially purified Tat-SF fraction inactivated Tat-SF transcriptional activity. C. Anti-pp140 antibody efficiently removed pp140 from the Tat-SF fraction.
Figure 4C:
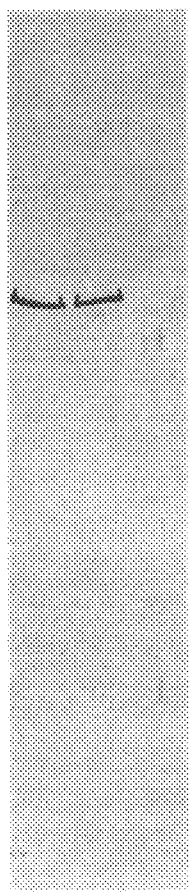

The 140 kD polypeptide was recovered from the SDS polyacrylamide gel by blotting onto a nitrocellulose membrane. Approximately 15 $\mu$g pp140 was recovered from the membrane and subjected to digestion with lys-C. Six major peptides were obtained and microsequenced. Sequence analysis of six peptides indicated that pp140 was a novel protein. However, one of the peptides (KMNAQETATGMAFEEPIDE, SEQ ID NO:3) was contained in the sequence of an unidentified "expressed sequence tag" (EST) EST60354 in the Washington University/Merck EST database. A 103 amino acid protein fragment (FIG. 5A, amino acids 387 to 489) encoded by the corresponding EST clone was expressed as a GST fusion and used to immunize rabbits for the production of polyclonal antisera. By Western blotting, the affinity-purified antibody specifically recognized a 140 kD protein present in both HeLa nuclear extracts and a partially purified Tat-SF fraction (FIG. 4C).

Example 4 pp140 and a Cellular Kinase Form a Complex Independently of Tat

The Tat-SF specific antibody was used to test the relationship between the EST clone and p140. The Tat-SF fraction was subjected to immunodepletion with the affinity purified antibody and then incubated together with the pc-D fraction and Tat. The polypeptide pp140 was immunodepleted from a 0.4–0.5 M KCl Q-Sepharose fraction (Tat-SF fraction) through incubation on ice twice for 1.5 hr each with the affinity purified anti-pp140 antibody immobilized on protein A Sepharose beads. Referring to FIG. 4, the depleted (lanes 5 and 6) or undepleted Tat-SF fractions (no depl. lanes 1–4) were incubated with the pc-D fraction in the absence (−) or presence (+) of Tat and the reactions were subjected to immunoprecipitation with the immobilized anti-pp140 antibody (lanes 3–6). Preimmune antibody was used in control precipitations (lanes 1 and 2). An unfractionated HeLa nuclear extract (NE) with (+) or without (−) the addition of Tat was also subjected to immunoprecipitation with the specific antibody (lanes 7 and 8). After extensive washes with buffer D containing 100 mM KCl, 0.1% NP-40, and 10 mM $MgCl_2$, the immune-complex bound to protein A Sepharose beads was analyzed in a kinase reaction in the presence of $\gamma$-$^{32}$P ATP for 10 min at 30° C., washed with buffer D, and analyzed by SDS-PAGE (FIG. 4A, lane 6). In contrast to the control undepleted Tat-SF fraction (lane 4), the fraction depleted with the specific antibody did not contain the phosphorylated pp140 (compare lanes 4 and 6). Therefore, the 140 kD protein recovered from the SDS gel and represented by the EST clone was indeed pp140, the kinase substrate.

These reactions also suggest that the polypeptide pp140 and its kinase formed a stable complex independently of Tat. When the Tat-SF fraction and the pc-D fraction were incubated together in the absence of Tat, followed by immunoprecipitation with the anti-pp140 antibody, pp140 was phosphorylated by its associated kinase when the isolated immune-complex was assayed in the kinase reaction (FIG. 4A, lane 3). This result indicates that pp140 forms a complex with its kinase in the absence of Tat. Furthermore, the addition of Tat to the initial incubation did not change the level of phosphorylation on pp140 (compare lanes 3 and 4).

A preformed complex containing pp140 and its kinase could be isolated by immunoprecipitation and detected in a kinase reaction from an unfractionated HeLa nuclear extract in the absence of Tat (FIG. 4A, compare lanes 7 and 8). This complex was stable under transcription conditions (less than 0.1 M KCl), but dissociated in washes of greater than 0.25 M KCl, and probably dissociated during fractionation in the purification of Tat-SF. These observations suggest that Tat is not required for the phosphorylation of pp140 by its associated kinase, but is required for the association of the phosphorylated pp140 and the kinase with TAR (FIG. 1B). Thus, Tat probably recruits a preformed complex containing pp140 and a kinase to the HIV promoter region during transcription.

Example 5 pp140 is Required for Tat-SF Transcriptional Activity

Figure 4B:
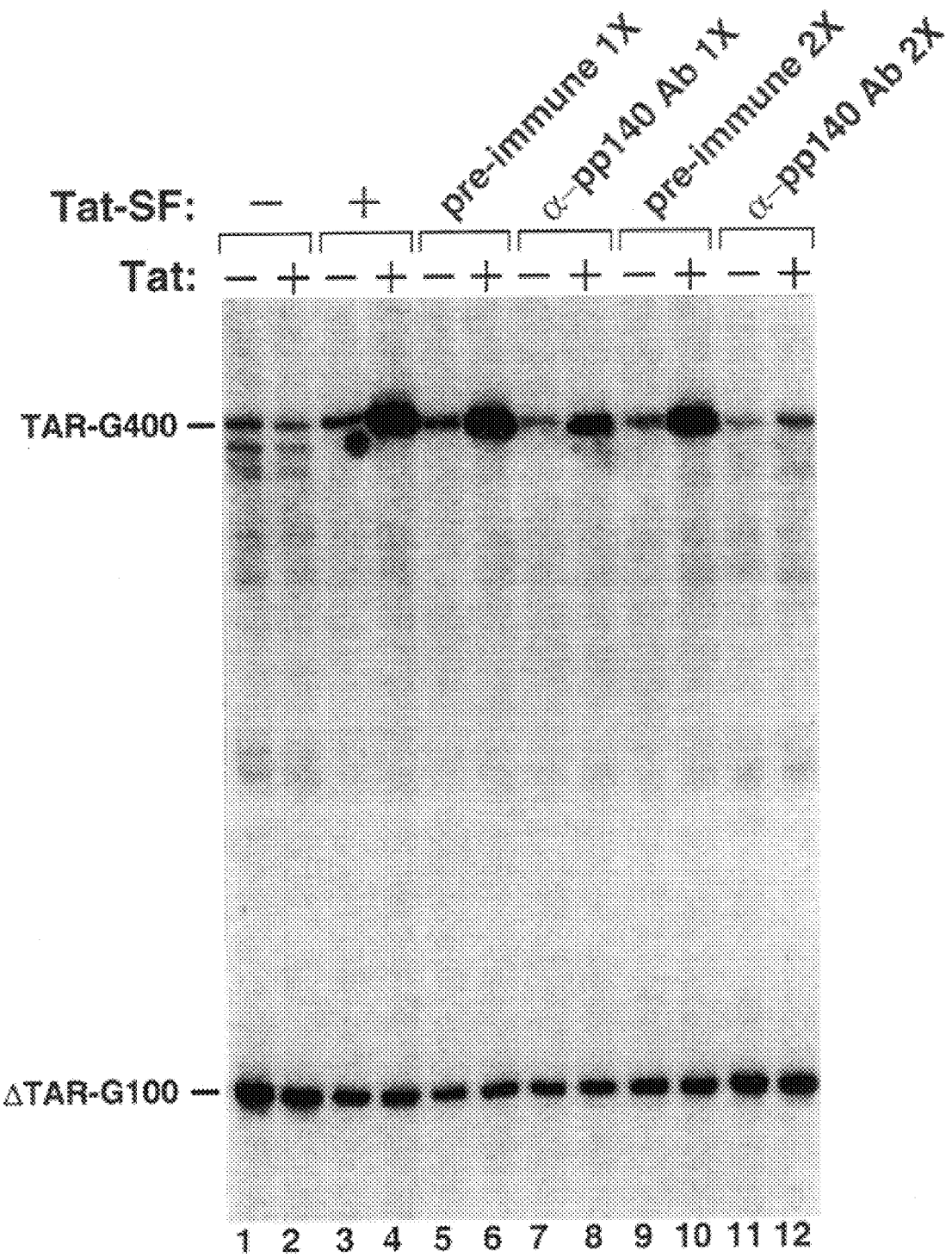

To test whether pp140 is indeed necessary for Tat activation, the anti-pp140 antibody was used to immunodeplete pp140 from a partially purified fraction containing Tat-SF activity and the depleted fraction was then tested in reconstituted transcription reactions for its ability to support Tat activation (FIG. 4B). A 0.4–0.5 M KCl Q-Sepharose fraction containing Tat-SF activity was subjected to immunodepletion with preimmune antibody (lanes 5, 6, 9, and 10) or specific anti-pp140 antibody (lanes 7, 8, 11, and 12) immobilized on protein A Sepharose beads as in Example 4. Tat-SF fraction subjected to depletion once (1×) or twice (2×), and the undepleted Tat-SF fraction (lanes 3 and 4) were tested in transcription reactions for Tat-SF activity as described above. No Tat-SF fraction was present in the control reactions (lanes 1 and 2). Control reactions without Tat-SF did not support Tat activation (FIG. 4B, lanes 1 and 2). Inclusion of the Tat-SF fraction resulted in a TAR-dependent activation by Tat as expected (lanes 3 and 4). As compared to control Tat-SF fraction (lanes 3 and 4). depletion of the Tat-SF fraction with specific anti-pp140 antibody immobilized on protein A Sepharose matrix either once (lanes 7 and 8) or especially twice (lanes 11 and 12) significantly reduced its ability to support Tat activation. In contrast, depletion of the Tat-SF fraction with preimmune antibody either once (lanes 5 and 6) or twice (lanes 9 and 10) did not significantly reduce Tat activation. Similarly, depletion of the Tat-SF fraction with an unrelated antibody (anti-HA mAb 12CA5) had no effect Tat activation.

The undepleted Tat-SF fraction and Tat-SF fraction twice-depleted with the specific or preimmune antibody were subjected to electrophoresis and Western blotting with the anti-pp140 antisera. As expected, a Western blot (FIG. 4C) indicates that depletion with the anti-pp140 antibody efficiently removed pp140 from Tat-SF fraction. Taken together, these experiments strongly argue that pp140 is indeed necessary for Tat-SF transcriptional activity.

Example 6

Isolation of the cDNA Encoding pp140

An XhoI-EcoRI fragment $^{32}$P-labeled DNA probe made from the insert of the EST clone corresponding to the COOH-terminus of the Tat-SF1 gene and its 3' untranslated region was labeled and used as a probe to screen a λZiplox (Gibco BRL) cDNA library prepared from human HL60 cells (provided by J. Borrow, MIT, Cambridge, Mass.). cDNAs were recovered from seven independent plaques in the autonomously-replicating plasmid pZL1 using the protocol provided by the manufacturer (Gibco BRL). Inserts from the seven independent plaques had similar restriction endonuclease cleavage patterns, and sequencing confirmed that they contained overlapping segments. The largest cDNA clone containing the full length Tat-SF1 gene was named pZL-Tat-SF1-4b and was sequenced by dideoxy-DNA sequencing with T7 DNA polymerase. The largest cDNA fragment was 2.8-kb in length and contained a 2271 -bp open reading frame. There were multiple in-frame stop codons both upstream and downstream of this coding region. Surprisingly, the open reading frame encoded a protein of 754 amino acids with a calculated molecular weight of 85,767 daltons (FIG. 5A), which was significantly less than the apparent molecular weight of 140 kD calculated from the mobility in an SDS polyacrylamide gel.

This cDNA was judged to encode the authentic full length pp140 based on several observations. First, transfection of this cDNA into human 293T cells (Pear et al., *Proc. Natl. Acad. Sci. USA* 90:8392–8396, 1993) resulted in the production of the full length pp140 polypeptide and thus a significant increase in the total cellular level of pp140 as judged by Western blotting. Second, all six peptide sequences obtained from partial sequencing of pp140 were found in the predicted coding region (underlined in FIG. 5). Third, Northern analysis of poly(A)$^-$ RNA isolated from several different types of human cells detected a single 3.0 kb species, a length consistent with that of the cDNA segment and adequate to encode a polypeptide of 86 kD. Finally, this cDNA and two additional cDNA clones isolated from a completely different cDNA library had identical upstream in-frame stop codons.

Sequence analysis of the protein, referred to as Tat-SF1, is shown in FIG. 5A. Glutamate (E) and aspartate (D)

residues present in the COOH-terminal half of Tat-SF1 (amino acids 420 to 754) are shown in bold face type. The two RNA recognition motifs (RRMs) in the NH$_2$-terminal half of Tat-SF1 are boxed, with the conserved RNP1 and RNP2 motifs shown in shaded area and bold face type, respectively. The six peptides of Tat-SF1 that were generated by digestion with lys-C and subjected to microsequencing are underlined. The regions of Tat-SF1 that are homologous to human EWS are underlined with broken lines.

The sequence analysis of the protein revealed that it has several unique features. The protein can be roughly divided at position 420 into two halves. The COOH-terminal half was extremely rich in acidic amino acids, with 48% of the last 245 amino acid residues as glutamate or aspartate. The unusual acidic nature of this protein may be responsible for its aberrant mobility in an SDS gel. The COOH-terminal half also contained many serine residues that are arranged in a short peptide sequence matching consensus sites for phosphorylation by Casein Kinase II (Marshak and Carroll, *Methods Enzymol.* 200:134–156, 1991). Such phosphorylation would contribute more negative charges to this region.

The NH$_2$-terminal half of Tat-SF1 contained two tandem RNA recognition motifs (Kenan et al., *Trends Biochem. Sci.* 16:214–220, 1991) which have homology to many RNA-binding proteins. Interestingly, the first RRM of Tat-SF1 (amino acid 128 to 217, boxed in FIG. 5A) was similar in length and displayed the strongest sequence homology to the RRMs located in the COOH-terminal half of two closely related human proteins, EWS (Delattre et al., *Nature* 359:162–165, 1992; Sorensen et al., *Nature Genet.* 6:146–151, 1994) (FIG. 5B) and FUS/TLS (Crozat et al., *Nature* 363:640–644, 1993; Rabbitts et al., *Nature Genet.* 4:175–180, 1993). Furthermore, the sequence homology between Tat-SF1 and EWS, or between Tat-SF1 and FUS/TLS, extended beyond the two RRMs into the immediate NH$_2$-terminal region of Tat-SF1 (FIGS. 5A and B). The amino acid sequences of the homologous regions of Tat-SF1 (SEQ ID NO:2) and EWS (SEQ ID NO:4) are compared in FIG. 5B. The amino acids of each protein are numbered next to the sequences. Vertical lines and dots indicate identical and conserved residues, respectively. EWS has two tandem, imperfect repeats (amino acids 209 to 236) that show homology to Tat-SF1 (amino acids 30 to 44). The alignment between the first repeat (amino acids 209–223) of EWS and Tat-SF1 is shown. The first RRM of Tat-SF1 (amino acids 128 to 446) is almost identical in length, and is 27% identical and 52% similar in amino acid sequence to the RRM of EWS. Sequence homology similar to that observed between Tat-SF1 and EWS also exists between Tat-SF1 and human FUS/TLS, which is closely related to EWS. The RRMs of other RNA binding proteins are less homologous and show greater variations in length as revealed by the BLAST algorithm (Altschul et al., *J. Mol. Biol.* 215:403–410, 1990).

These observations suggest that Tat-SF1 is related to EWS and FUS/TLS, which are members of a novel class of putative transcription factors that presumably interact with RNA. Both EWS and FUS/TLS are involved in many forms of human solid tumors (Ladanyi, *Diagn. Mol. Pathol.* 4:162–173, 1995; Rabbitts, *Nature* 372:143–149, 1994), such as Ewing's sarcoma (Delattre et al., 1992; Sorensen et al., 1994) and human myxoid liposarcoma (Crozat et al., 1993; Rabbitts et al., 1993), through chromosomal translocations.

Example 7

Overexpression of Tat-SF1 Enhances Tat Activation In Vivo

Figures 6A, 6B:
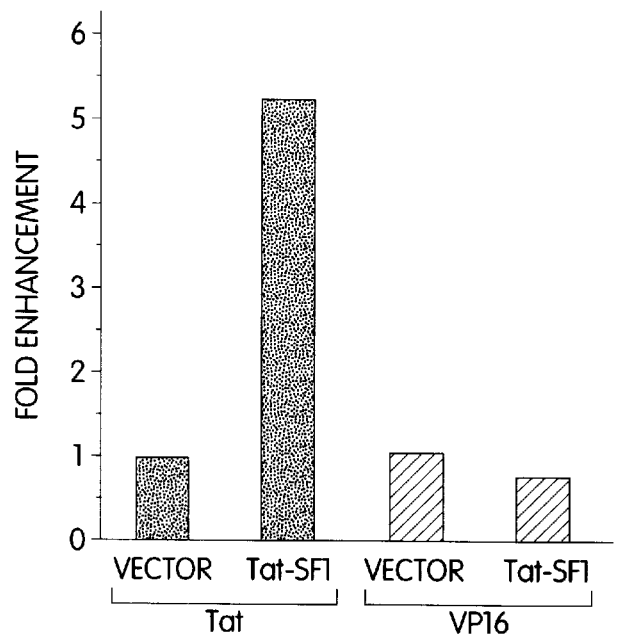
FIG. 6 shows that overexpression of Tat-SF1 enhances Tat activation in HeLa cells.

To investigate whether overexpression of Tat-SF1 affects the level of Tat activation in vivo, a plasmid expressing Tat-SF1 and a reporter construct containing HIV-1 LTR linked to the bacterial CAT gene were introduced into HeLa cells either in the presence or absence of a cotransfected plasmid expressing Tat (Table I and FIG. 6). As a control, the effect of Tat-SF1 overexpression on transcriptional activation by the acidic activation domain VP16 in the TFEB-VP16 and GAL4-VP16 fusion proteins was assayed (Harper et al., *Proc. Natl. Acad. Sci. USA* 93:8536–8540, 1996). The Tat-SF1 gene was subcloned into the mammalian expressing vector pSV7d (Truett et al., *DNA* 4:333–349, 1985) to create pSV-Tat-SF1. pSV-Tat-SF1 or vector pSV7d and a reporter construct pBennCAT (Gendelman et al., *Proc. Natl. Acad. Sci. USA* 83:9759–63, 1986) containing HIV-1 LTR linked to the bacterial CAT gene (1 μg each) and an internal control plasmid pCMVβ-Gal were co-transfected into HeLa cells, either in the presence or absence of a Tat expressing plasmid pcTat (0.3 μg) (Tiley et al., *Virology* 178:560–567, 1990). CAT activity was measured 48 hr later as described (Neumann et al., *BioTechniques* 5:444–447, 1987). In control experiments, pSV-Tat-SF1 or pSV7d and the reporter construct pMyc3E1BLuc (Harper et al., 1996) were introduced into HeLa cells together with the plasmids pRCCMV-TFEB-VP16 (0.3 μg) expressing the TFEB-VP16 fusion protein (Harper et al., 1996). pMyc3E1BLuc contained the luciferase gene downstream of the Adenovirus E1B promoter with three binding sites for TFEB. Reporter construct pG5E1BCAT (Lillie et al., *Nature* 338:39–44, 1989) containing five GAL4-binding sites inserted upstream of the E1B promoter and the CAT gene was used to assay GAL4-VP16 trans-activation. The fold activation by Tat or VP16 in cells containing the empty vector was assigned a value of 1, and activation in the presence of Tat-SF1 was adjusted accordingly. The mean value from three experiments was shown.

Expression of Tat-SF1 from the transfected DNA consistently resulted in an increase in Tat activation by an average of 5.2-fold as compared to the control HeLa cells transfected with an empty vector (FIG. 6 and Table I). The enhanced activation mediated by Tat-SF1 was Tat-specific, since overexpression of Tat-SF1 had little, or sometimes even a slightly negative, effect on transcriptional activation by TFEB-VP16. Interestingly, the elevated fold induction by Tat resulting from Tat-SF1 overexpression was caused by a combination of a decrease in the basal level of transcription from HIV-1 LTR in the absence of Tat and a small increase in the level of Tat-activated transcription (Table I). Since Tat-SF1 is probably a component of a protein complex that also includes a cellular kinase and perhaps other cellular components, overexpression of Tat-SF1 alone may disrupt the normal stoichiometry of the complex resulting in a decrease in the basal level of HIV transcription. The presence of Tat could stabilize and recruit the active form of the complex to the HIV promoter to stimulate the processivity of elongation.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

A Sequence Listing is presented below and is followed by what is claimed:

What is claimed is:

1. An isolated nucleic acid molecule encoding a Tat-Stimulatory Factor protein selected from the group consisting of
   (a) nucleic acid molecules which hybridize under stringent conditions to a molecule consisting of tie coding region of the nucleic acid sequence of SEQ ID NO:1 and which codes for the Tat-Stimulatory Factor protein,
   (b) nucleic acid molecules that differ from the nucleic acid molecules of (a) in codon sequence due to the degeneracy of the genetic code, and
   (c) complements of (a) and (b).

2. The isolated nucleic acid molecule of claim 1, wherein the isolated nucleic acid molecule comprises the coding region of SEQ ID NO:1.

3. The isolated nucleic acid molecule of claim 1, wherein the isolated nucleic acid molecule consists of the coding region of SEQ ID NO:1.

4. An isolated nucleic acid molecule selected from the group consisting of (a) a unique fragment of SEQ ID NO:1 between 12 and 2650 nucleotides in length, and (b) complements of (a).

5. The isolated nucleic acid molecule of claim 4, wherein the isolated nucleic acid molecule is a unique fragment of the coding region of SEQ ID NO:1 and wherein the isolated nucleic acid molecule is selected from the group consisting of at least 14 contiguous nucleotides of SEQ ID NO:1, and (b) complements of (a).

6. The isolated nucleic acid molecule of claim 4, wherein the isolated nucleic acid molecule is selected from the group consisting of (a) at least 15 contiguous nucleotides of SEQ ID NO:1, and (b) complements of (a).

7. The isolated nucleic acid molecule of claim 4, wherein the isolated nucleic acid molecule is selected from the group consisting of (a) at least 16 contiguous nucleotides of SEQ ID NO:1, and (b) complements of (a).

8. The isolated nucleic acid molecule of claim 4, wherein the isolated nucleic acid molecule is selected from the group consisting of (a) at least 17 contiguous nucleotides of SEQ ID NO:1, and (b) complements of (a).

9. The isolated nucleic acid molecule of claim 4, wherein the isolated nucleic acid molecule is selected from the group consisting of (a) at least 18 contiguous nucleotides of SEQ ID NO.:1, and (b) complements of (a).

10. The isolated nucleic acid molecule of claim 4, wherein the isolated nucleic acid molecule is selected from the group consisting of (a) at least 20 contiguous nucleotides of SEQ ID NO:1, and (b) complements of (a).

11. The isolated nucleic acid molecule of claim 4, wherein the isolated nucleic acid molecule is selected from the group consisting of (a) at least 22 contiguous nucleotides of SEQ ID NO:1, and (b) complements of (a).

12. The isolated nucleic acid molecule of claim 4, wherein the isolated nucleic acid molecule is selected from the group consisting of (a) between 12 and 32 contiguous nucleotides of SEQ ID NO:1, and (b) complements of (a).

13. A host cell transformed or transfected with an expression vector comprising the isolated nucleic acid molecule of any of claims 1, 2 or 3, operably linked to a promoter.

* * * * *

SEQUENCE LISTING

<160> NUMBER OF SEQ ID NOS: 5

<210> SEQ ID NO 1
<211> LENGTH: 2815
<212> TYPE: DNA
<213> ORGANISM: Homo sapiens
<220> FEATURE:
<221> NAME/KEY: CDS
<222> LOCATION: 110..2371
<221> NAME/KEY: unsure
<222> LOCATION: 46..46
<223> OTHER INFORMATION: n = a, c, g or t
<221> NAME/KEY: unsure
<222> LOCATION: 2731..2731
<223> OTHER INFORMATION: n = a, c, g or t

<400> SEQUENCE: 1

```
gggaaagctg gtacgcctgc aggtaccggt ccggaattcc ggccgngtcg aaagcgtcat      60
ttcggcctct tagttcttct gaaccctgct cctgagctag gtaggaaac atg agc ggc     118
                                                    Met Ser Gly
                                                      1 acc aac ttg gat ggg aac gat gag ttt gat gag cag ttg cga atg caa      166
Thr Asn Leu Asp Gly Asn Asp Glu Phe Asp Glu Gln Leu Arg Met Gln
      5                  10                  15 gaa ttg tac gga gac ggc aag gat ggt gac acc cag acc gat gcc ggc      214
Glu Leu Tyr Gly Asp Gly Lys Asp Gly Asp Thr Gln Thr Asp Ala Gly
 20                  25                  30                  35 gga gaa ccc gat tct ctc ggg cag cag ccg acg gac act ccc tac gag      262
Gly Glu Pro Asp Ser Leu Gly Gln Gln Pro Thr Asp Thr Pro Tyr Glu
                 40                  45                  50 tgg gac ctg gac aaa aag gct tgg ttc ccc aag att act gaa gat ttc      310
Trp Asp Leu Asp Lys Lys Ala Trp Phe Pro Lys Ile Thr Glu Asp Phe
         55                  60                  65 att gct aca tat cag gcc aat tat ggc ttc tct aac gat ggc gca tct      358
Ile Ala Thr Tyr Gln Ala Asn Tyr Gly Phe Ser Asn Asp Gly Ala Ser
     70                  75                  80 agt tct acc gca aat gtt gaa gat gtc cat gct agg act gca gag gaa      406
Ser Ser Thr Ala Asn Val Glu Asp Val His Ala Arg Thr Ala Glu Glu
 85                  90                  95 cct cca caa gaa aaa gcc ccg gaa ccc act gat gcc aga aag aag gga      454
Pro Pro Gln Glu Lys Ala Pro Glu Pro Thr Asp Ala Arg Lys Lys Gly
100                 105                 110                 115 gaa aaa aga aag gct gag tca gga tgg ttt cat gtt gaa gaa gac aga      502
Glu Lys Arg Lys Ala Glu Ser Gly Trp Phe His Val Glu Glu Asp Arg
                 120                 125                 130 aat aca aat gta tac gtg tct ggt ttg cct cca gat att aca gtg gat      550
Asn Thr Asn Val Tyr Val Ser Gly Leu Pro Pro Asp Ile Thr Val Asp
         135                 140                 145 gaa ttt ata caa ctt atg tcc aag ttt ggc att att atg aga gat cct      598
Glu Phe Ile Gln Leu Met Ser Lys Phe Gly Ile Ile Met Arg Asp Pro
     150                 155                 160 cag aca gaa gaa ttt aag gtc aaa ctt tac aaa gat aat caa gga aat      646
Gln Thr Glu Glu Phe Lys Val Lys Leu Tyr Lys Asp Asn Gln Gly Asn
 165                 170                 175 ctt aaa gga gac ggt ctt tgc tgt tat ttg aaa aga gaa tct gtg gaa      694
Leu Lys Gly Asp Gly Leu Cys Cys Tyr Leu Lys Arg Glu Ser Val Glu
180                 185                 190                 195 ctt gca tta aaa ctt ttg gat gaa gat gaa att aga ggc tac aaa tta      742
Leu Ala Leu Lys Leu Leu Asp Glu Asp Glu Ile Arg Gly Tyr Lys Leu
                 200                 205                 210
```

```
cat gtt gag gtg gca aag ttt caa ctg aag gga gaa tat gat gcc tca     790
His Val Glu Val Ala Lys Phe Gln Leu Lys Gly Glu Tyr Asp Ala Ser
            215                 220                 225 aag aag aag aag aag tgc aaa gac tat aag aag aag ctg tct atg caa     838
Lys Lys Lys Lys Lys Cys Lys Asp Tyr Lys Lys Lys Leu Ser Met Gln
        230                 235                 240 caa aag cag ttg gat tgg aga cct gag agg cga gcc gga cca tcc cgg     886
Gln Lys Gln Leu Asp Trp Arg Pro Glu Arg Arg Ala Gly Pro Ser Arg
    245                 250                 255 atg cgc cat gag cga gtt gtc atc atc aag aat atg ttt cat cct atg     934
Met Arg His Glu Arg Val Val Ile Ile Lys Asn Met Phe His Pro Met
260                 265                 270                 275 gat ttt gag gat gat ccg ttg gtg ctg aat gag atc aga gaa gac ctt     982
Asp Phe Glu Asp Asp Pro Leu Val Leu Asn Glu Ile Arg Glu Asp Leu
                280                 285                 290 cga gta gag tgt tcg aag ttt gga caa att agg aaa ctc ctt ctc ttt    1030
Arg Val Glu Cys Ser Lys Phe Gly Gln Ile Arg Lys Leu Leu Leu Phe
            295                 300                 305 gat agg cac cca gat ggt gtg gcc tct gtg tcc ttt cgg gat cca gag    1078
Asp Arg His Pro Asp Gly Val Ala Ser Val Ser Phe Arg Asp Pro Glu
        310                 315                 320 gaa gct gat tat tgt att cag act ctc gat gga aga tgg ttt ggt ggc    1126
Glu Ala Asp Tyr Cys Ile Gln Thr Leu Asp Gly Arg Trp Phe Gly Gly
    325                 330                 335 cgt caa atc act gcc cag gca tgg gat ggg act aca gat tat cag gtg    1174
Arg Gln Ile Thr Ala Gln Ala Trp Asp Gly Thr Thr Asp Tyr Gln Val
340                 345                 350                 355 gag gaa acc tca aga gaa agg gag gaa agg ctg aga gga tgg gag gct    1222
Glu Glu Thr Ser Arg Glu Arg Glu Glu Arg Leu Arg Gly Trp Glu Ala
                360                 365                 370 ttc ctc aat gct cct gag gcc aac aga ggc ctt agc gtt cag att ctg    1270
Phe Leu Asn Ala Pro Glu Ala Asn Arg Gly Leu Ser Val Gln Ile Leu
            375                 380                 385 tct ctg ctt cga aag gca ggg cct tct aga gca agg cat ttt tca gag    1318
Ser Leu Leu Arg Lys Ala Gly Pro Ser Arg Ala Arg His Phe Ser Glu
        390                 395                 400 cac ccc agc aca tct aaa atg aat gct caa gaa act gca act gga atg    1366
His Pro Ser Thr Ser Lys Met Asn Ala Gln Glu Thr Ala Thr Gly Met
    405                 410                 415 gca ttt gaa gaa cct ata gat gag aag aag ttt gaa aag aca gaa gat    1414
Ala Phe Glu Glu Pro Ile Asp Glu Lys Lys Phe Glu Lys Thr Glu Asp
420                 425                 430                 435 ggg gga gaa ttt gaa gaa ggt gct tct gaa aac aat gct aag gaa agt    1462
Gly Gly Glu Phe Glu Glu Gly Ala Ser Glu Asn Asn Ala Lys Glu Ser
                440                 445                 450 agc ccc gaa aaa gag gct gaa gaa ggc tgc cct gaa aaa gaa tct gaa    1510
Ser Pro Glu Lys Glu Ala Glu Glu Gly Cys Pro Glu Lys Glu Ser Glu
            455                 460                 465 gag ggc tgc ccc aaa aga ggg ttt gaa ggc agc tgc tcc caa aaa gag    1558
Glu Gly Cys Pro Lys Arg Gly Phe Glu Gly Ser Cys Ser Gln Lys Glu
        470                 475                 480 tct gaa gaa ggc aat ccc gta aga gga tct gaa gag gat agt cct aaa    1606
Ser Glu Glu Gly Asn Pro Val Arg Gly Ser Glu Glu Asp Ser Pro Lys
    485                 490                 495 aaa gag tct aaa aag aag aca ctc aaa aat gat tgt gaa gag aat ggc    1654
Lys Glu Ser Lys Lys Lys Thr Leu Lys Asn Asp Cys Glu Glu Asn Gly
500                 505                 510                 515 ctt gca aag gaa tct gaa gat gac ctc aac aag gag tct gaa gag gag    1702
Leu Ala Lys Glu Ser Glu Asp Asp Leu Asn Lys Glu Ser Glu Glu Glu
                520                 525                 530
```

-continued

```
gtt ggc ccc aca aaa gag tcc gaa gaa gat gac tca gag aaa gag tct      1750
Val Gly Pro Thr Lys Glu Ser Glu Glu Asp Asp Ser Glu Lys Glu Ser
            535                 540                 545 gat gaa gac tgc tct gaa aaa cag tct gaa gat ggc tcc gaa aga gaa      1798
Asp Glu Asp Cys Ser Glu Lys Gln Ser Glu Asp Gly Ser Glu Arg Glu
        550                 555                 560 ttt gaa gaa aat ggt ctc gag aaa gat ttg gac gag gaa ggt tct gaa      1846
Phe Glu Glu Asn Gly Leu Glu Lys Asp Leu Asp Glu Glu Gly Ser Glu
    565                 570                 575 aag gag ctt cat gaa aat gtt ctt gac aaa gag tta gaa gaa aat gac      1894
Lys Glu Leu His Glu Asn Val Leu Asp Lys Glu Leu Glu Glu Asn Asp
580                 585                 590                 595 tct gaa aac tcc gaa ttt gaa gat gac ggc tct gaa aaa gtg tta gat      1942
Ser Glu Asn Ser Glu Phe Glu Asp Asp Gly Ser Glu Lys Val Leu Asp
            600                 605                 610 gag gaa ggc tct gag aga gag ttt gac gaa gat tca gat gaa aag gaa      1990
Glu Glu Gly Ser Glu Arg Glu Phe Asp Glu Asp Ser Asp Glu Lys Glu
        615                 620                 625 gaa gag gag gat aca tat gaa aaa gta ttt gat gat gag tct gat gag      2038
Glu Glu Glu Asp Thr Tyr Glu Lys Val Phe Asp Asp Glu Ser Asp Glu
    630                 635                 640 aaa gag gat gaa gaa tat gca gat gaa aag ggg ctt gaa gct gct gat      2086
Lys Glu Asp Glu Glu Tyr Ala Asp Glu Lys Gly Leu Glu Ala Ala Asp
645                 650                 655 aaa aag gcg gaa gaa ggt gat gca gat gaa aag ctg ttt gaa gag tca      2134
Lys Lys Ala Glu Glu Gly Asp Ala Asp Glu Lys Leu Phe Glu Glu Ser
            660                 665                 670                 675 gat gac aag gaa gat gaa gat gca gat gga aag gaa gtt gaa gat gct      2182
Asp Asp Lys Glu Asp Glu Asp Ala Asp Gly Lys Glu Val Glu Asp Ala
        680                 685                 690 gac gaa aag ttg ttc gaa gat gat gat tcc aat gag aag ttg ttt gat      2230
Asp Glu Lys Leu Phe Glu Asp Asp Asp Ser Asn Glu Lys Leu Phe Asp
    695                 700                 705 gag gag gaa gat tcc agt gag aag ttg ttt gac gat tct gat gag agg      2278
Glu Glu Glu Asp Ser Ser Glu Lys Leu Phe Asp Asp Ser Asp Glu Arg
710                 715                 720 ggg act ttg ggt ggt ttt ggg agt gtt gaa gaa ggg ccc cta tcc act      2326
Gly Thr Leu Gly Gly Phe Gly Ser Val Glu Glu Gly Pro Leu Ser Thr
            725                 730                 735 ggc agc agc ttt att ctc agt agc gat gat gat gac gat gat att taatc    2376
Gly Ser Ser Phe Ile Leu Ser Ser Asp Asp Asp Asp Asp Asp Ile
        740                 745                 750 ccttaaactt gctttttagg gagagtcctc catctacatt tgcctgtgct tcagggtaat    2436
tactagtagt gttacatgaa catgtgcata gtggtaggat gccatcagat taaagcattg    2496
aagtgtttca ttgttacctg tacctaatgg ttttaaatat atgttaattg attgtttagt    2556
taaaatgtca tagttacaat gcaagtaaac tggatacttg ttcttttgtc agatttgtta    2616
aatgcatgca gaataatatt tttaagagta ttgattgaag tttgtgatat tcatcaataa    2676
aaatgagttg ataatatgca gaaactgaaa aaaaaaaaa aaaaaaagt cgacncggcc      2736 ggaattcccg ggtcgacgag ctcactagtc ggcggccgct ctagaggatc caagcttacg    2796
tacgcgtgca tgcgacgtc                                                 2815
```

<210> SEQ ID NO 2
<211> LENGTH: 754
<212> TYPE: PRT
<213> ORGANISM: Homo sapiens -continued

<400> SEQUENCE: 2

```
Met Ser Gly Thr Asn Leu Asp Gly Asn Asp Glu Phe Asp Glu Gln Leu
 1               5                  10                  15

Arg Met Gln Glu Leu Tyr Gly Asp Gly Lys Asp Gly Asp Thr Gln Thr
            20                  25                  30

Asp Ala Gly Gly Glu Pro Asp Ser Leu Gly Gln Gln Pro Thr Asp Thr
        35                  40                  45

Pro Tyr Glu Trp Asp Leu Asp Lys Lys Ala Trp Phe Pro Lys Ile Thr
 50                  55                  60

Glu Asp Phe Ile Ala Thr Tyr Gln Ala Asn Tyr Gly Phe Ser Asn Asp
 65                  70                  75                  80

Gly Ala Ser Ser Ser Thr Ala Asn Val Glu Asp Val His Ala Arg Thr
                85                  90                  95

Ala Glu Glu Pro Pro Gln Glu Lys Ala Pro Glu Pro Thr Asp Ala Arg
            100                 105                 110

Lys Lys Gly Glu Lys Arg Lys Ala Glu Ser Gly Trp Phe His Val Glu
        115                 120                 125

Glu Asp Arg Asn Thr Asn Val Tyr Val Ser Gly Leu Pro Pro Asp Ile
130                 135                 140

Thr Val Asp Glu Phe Ile Gln Leu Met Ser Lys Phe Gly Ile Ile Met
145                 150                 155                 160

Arg Asp Pro Gln Thr Glu Glu Phe Lys Val Lys Leu Tyr Lys Asp Asn
                165                 170                 175

Gln Gly Asn Leu Lys Gly Asp Gly Leu Cys Cys Tyr Leu Lys Arg Glu
            180                 185                 190

Ser Val Glu Leu Ala Leu Lys Leu Leu Asp Glu Asp Glu Ile Arg Gly
        195                 200                 205

Tyr Lys Leu His Val Glu Val Ala Lys Phe Gln Leu Lys Gly Glu Tyr
210                 215                 220

Asp Ala Ser Lys Lys Lys Lys Cys Lys Asp Tyr Lys Lys Lys Leu
225                 230                 235                 240

Ser Met Gln Gln Lys Gln Leu Asp Trp Arg Pro Glu Arg Arg Ala Gly
                245                 250                 255

Pro Ser Arg Met Arg His Glu Arg Val Val Ile Ile Lys Asn Met Phe
            260                 265                 270

His Pro Met Asp Phe Glu Asp Asp Pro Leu Val Leu Asn Glu Ile Arg
        275                 280                 285

Glu Asp Leu Arg Val Glu Cys Ser Lys Phe Gly Gln Ile Arg Lys Leu
290                 295                 300

Leu Leu Phe Asp Arg His Pro Asp Gly Val Ala Ser Val Ser Phe Arg
305                 310                 315                 320

Asp Pro Glu Glu Ala Asp Tyr Cys Ile Gln Thr Leu Asp Gly Arg Trp
                325                 330                 335

Phe Gly Gly Arg Gln Ile Thr Ala Gln Ala Trp Asp Gly Thr Thr Asp
            340                 345                 350

Tyr Gln Val Glu Glu Thr Ser Arg Glu Arg Glu Arg Leu Arg Gly
        355                 360                 365

Trp Glu Ala Phe Leu Asn Ala Pro Glu Ala Asn Arg Gly Leu Ser Val
370                 375                 380

Gln Ile Leu Ser Leu Leu Arg Lys Ala Gly Pro Ser Arg Ala Arg His
385                 390                 395                 400

Phe Ser Glu His Pro Ser Thr Ser Lys Met Asn Ala Gln Glu Thr Ala
                405                 410                 415
```

```
Thr Gly Met Ala Phe Glu Glu Pro Ile Asp Glu Lys Lys Phe Glu Lys
            420                 425                 430

Thr Glu Asp Gly Gly Glu Phe Glu Gly Ala Ser Glu Asn Asn Ala
            435                 440                 445

Lys Glu Ser Ser Pro Glu Lys Glu Ala Glu Glu Gly Cys Pro Glu Lys
            450                 455                 460

Glu Ser Glu Glu Gly Cys Pro Lys Arg Gly Phe Glu Gly Ser Cys Ser
465                 470                 475                 480

Gln Lys Glu Ser Glu Gly Asn Pro Val Arg Gly Ser Glu Asp
                    485                 490                 495

Ser Pro Lys Lys Glu Ser Lys Lys Lys Thr Leu Lys Asn Asp Cys Glu
                500                 505                 510

Glu Asn Gly Leu Ala Lys Glu Ser Glu Asp Leu Asn Lys Glu Ser
            515                 520                 525

Glu Glu Glu Val Gly Pro Thr Lys Glu Ser Glu Asp Asp Ser Glu
            530                 535                 540

Lys Glu Ser Asp Glu Asp Cys Ser Glu Lys Gln Ser Glu Asp Gly Ser
545                 550                 555                 560

Glu Arg Glu Phe Glu Glu Asn Gly Leu Glu Lys Asp Leu Asp Glu Glu
                    565                 570                 575

Gly Ser Glu Lys Glu Leu His Glu Asn Val Leu Asp Lys Glu Leu Glu
                    580                 585                 590

Glu Asn Asp Ser Glu Asn Ser Glu Phe Glu Asp Gly Ser Glu Lys
            595                 600                 605

Val Leu Asp Glu Glu Gly Ser Glu Arg Glu Phe Asp Glu Asp Ser Asp
            610                 615                 620

Glu Lys Glu Glu Glu Glu Asp Thr Tyr Glu Lys Val Phe Asp Glu
625                 630                 635                 640

Ser Asp Glu Lys Glu Asp Glu Glu Tyr Ala Asp Glu Lys Gly Leu Glu
                    645                 650                 655

Ala Ala Asp Lys Lys Ala Glu Glu Gly Asp Ala Asp Glu Lys Leu Phe
            660                 665                 670

Glu Glu Ser Asp Asp Lys Glu Asp Glu Asp Ala Asp Gly Lys Glu Val
            675                 680                 685

Glu Asp Ala Asp Glu Lys Leu Phe Glu Asp Asp Ser Asn Glu Lys
690                 695                 700

Leu Phe Asp Glu Glu Asp Ser Ser Glu Lys Leu Phe Asp Asp Ser
705                 710                 715                 720

Asp Glu Arg Gly Thr Leu Gly Gly Phe Gly Ser Val Glu Glu Gly Pro
            725                 730                 735

Leu Ser Thr Gly Ser Ser Phe Ile Leu Ser Ser Asp Asp Asp Asp
            740                 745                 750

Asp Ile

<210> SEQ ID NO 3
<211> LENGTH: 19
<212> TYPE: PRT
<213> ORGANISM: Homo sapiens

<400> SEQUENCE: 3

Lys Met Asn Ala Gln Glu Thr Ala Thr Gly Met Ala Phe Glu Glu Pro
  1               5                  10                  15

Ile Asp Glu
```

```
<210> SEQ ID NO 4

<211> LENGTH: 656
<212> TYPE: PRT
<213> ORGANISM: Homo sapiens

<400> SEQUENCE: 4

Met Ala Ser Thr Asp Tyr Ser Thr Tyr Ser Gln Ala Ala Gln Gln
 1               5                  10                  15

Gly Tyr Ser Ala Tyr Thr Ala Gln Pro Thr Gln Gly Tyr Ala Gln Thr
                20                  25                  30

Thr Gln Ala Tyr Gly Gln Gln Ser Tyr Gly Thr Tyr Gly Gln Pro Thr
            35                  40                  45

Asp Val Ser Tyr Thr Gln Ala Gln Thr Thr Ala Thr Tyr Gly Gln Thr
50                  55                  60

Ala Tyr Ala Thr Ser Tyr Gly Gln Pro Pro Thr Gly Tyr Thr Thr Pro
65                  70                  75                  80

Thr Ala Pro Gln Ala Tyr Ser Gln Pro Val Gln Gly Tyr Gly Thr Gly
                85                  90                  95

Ala Tyr Asp Thr Thr Thr Ala Thr Val Thr Thr Thr Gln Ala Ser Tyr
            100                 105                 110

Ala Ala Gln Ser Ala Tyr Gly Thr Gln Pro Ala Tyr Pro Ala Tyr Gly
        115                 120                 125

Gln Gln Pro Ala Ala Thr Ala Pro Thr Arg Pro Gln Asp Gly Asn Lys
    130                 135                 140

Pro Thr Glu Thr Ser Gln Pro Gln Ser Ser Thr Gly Gly Tyr Asn Gln
145                 150                 155                 160

Pro Ser Leu Gly Tyr Gly Gln Ser Asn Tyr Ser Tyr Pro Gln Val Pro
                165                 170                 175

Gly Ser Tyr Pro Met Gln Pro Val Thr Ala Pro Pro Ser Tyr Pro Pro
            180                 185                 190

Thr Ser Tyr Ser Ser Thr Gln Pro Thr Ser Tyr Asp Gln Ser Ser Tyr
        195                 200                 205

Ser Gln Gln Asn Thr Tyr Gly Gln Pro Ser Ser Tyr Gly Gln Gln Ser
    210                 215                 220

Ser Tyr Gly Gln Gln Ser Ser Tyr Gly Gln Gln Pro Pro Thr Ser Tyr
225                 230                 235                 240

Pro Pro Gln Thr Gly Ser Tyr Ser Gln Ala Pro Ser Gln Tyr Ser Gln
                245                 250                 255

Gln Ser Ser Ser Tyr Gly Gln Gln Ser Ser Phe Arg Gln Asp His Pro
            260                 265                 270

Ser Ser Met Gly Val Tyr Gly Gln Glu Ser Gly Gly Phe Ser Gly Pro
        275                 280                 285

Gly Glu Asn Arg Ser Met Ser Gly Pro Asp Asn Arg Gly Arg Gly Arg
    290                 295                 300

Gly Gly Phe Asp Arg Gly Gly Met Ser Arg Gly Gly Arg Gly Gly Gly
305                 310                 315                 320

Arg Gly Gly Met Gly Ser Ala Gly Glu Arg Gly Gly Phe Asn Lys Pro
                325                 330                 335

Gly Gly Pro Met Asp Glu Gly Pro Asp Leu Asp Leu Gly Pro Pro Val
            340                 345                 350

Asp Pro Asp Glu Asp Ser Asp Asn Ser Ala Ile Tyr Val Gln Gly Leu
        355                 360                 365

Asn Asp Ser Val Thr Leu Asp Asp Leu Ala Asp Phe Phe Lys Gln Cys
```

-continued

```
                370                 375                 380
Gly Val Val Lys Met Asn Lys Arg Thr Gly Gln Pro Met Ile His Ile
385                 390                 395                 400
Tyr Leu Asp Lys Glu Thr Gly Lys Pro Lys Gly Asp Ala Thr Val Ser
                405                 410                 415
Tyr Glu Asp Pro Pro Thr Ala Lys Ala Ala Val Glu Trp Phe Asp Gly
                420                 425                 430
Lys Asp Phe Gln Gly Ser Lys Leu Lys Val Ser Leu Ala Arg Lys Lys
                435                 440                 445
Pro Pro Met Asn Ser Met Arg Gly Gly Leu Pro Pro Arg Glu Gly Arg
    450                 455                 460
Gly Met Pro Pro Leu Arg Gly Gly Pro Gly Pro Gly Gly Pro
465                 470                 475                 480
Gly Gly Pro Met Gly Arg Met Gly Gly Arg Gly Gly Asp Arg Gly
                485                 490                 495
Phe Pro Pro Arg Gly Pro Arg Gly Ser Arg Gly Asn Pro Ser Gly Gly
                500                 505                 510
Gly Asn Val Gln His Arg Ala Gly Asp Trp Gln Cys Pro Asn Pro Gly
                515                 520                 525
Cys Gly Asn Gln Asn Phe Ala Trp Arg Thr Glu Cys Asn Gln Cys Lys
530                 535                 540
Ala Pro Lys Pro Glu Gly Phe Leu Pro Pro Phe Pro Pro Gly
545                 550                 555                 560
Gly Asp Arg Gly Arg Gly Gly Pro Gly Gly Met Arg Gly Gly Arg Gly
                565                 570                 575
Gly Leu Met Asp Arg Gly Gly Pro Gly Gly Met Phe Arg Gly Gly Arg
                580                 585                 590
Gly Gly Asp Arg Gly Gly Phe Arg Gly Gly Arg Gly Met Asp Arg Gly
                595                 600                 605
Gly Phe Gly Gly Gly Arg Arg Gly Pro Gly Gly Pro Pro Gly Pro
    610                 615                 620
Leu Met Glu Gln Met Gly Gly Arg Arg Gly Gly Arg Gly Gly Pro Gly
625                 630                 635                 640
Lys Met Asp Lys Gly Glu His Arg Gln Glu Arg Arg Asp Arg Pro Tyr
                645                 650                 655
```

<210> SEQ ID NO 5
<211> LENGTH: 2672
<212> TYPE: DNA
<213> ORGANISM: Homo sapiens
<220> FEATURE:
<221> NAME/KEY: CDS
<222> LOCATION: 58..2319

<400> SEQUENCE: 5

```
agcgtcattt cggcctctta gttcttctga accctgctcc tgagctaggt aggaaac atg    60
                                                                 Met
                                                                  1 agc ggc acc aac ttg gat ggg aac gat gag ttt gat gag cag ttg cga    108
Ser Gly Thr Asn Leu Asp Gly Asn Asp Glu Phe Asp Glu Gln Leu Arg
         5                  10                  15 atg caa gaa ttg tac gga gac ggc aag gat ggt gac acc cag acc gat    156
Met Gln Glu Leu Tyr Gly Asp Gly Lys Asp Gly Asp Thr Gln Thr Asp
     20                  25                  30 gcc ggc gga gaa ccc gat tct ctc ggg cag cag ccg acg gac act ccc    204
Ala Gly Gly Glu Pro Asp Ser Leu Gly Gln Gln Pro Thr Asp Thr Pro
 35                  40                  45
```

-continued

| | |
|---|---|
| tac gag tgg gac ctg gac aaa aag gct tgg ttc ccc aag att act gaa<br>Tyr Glu Trp Asp Leu Asp Lys Lys Ala Trp Phe Pro Lys Ile Thr Glu<br>50                          55                        60                        65 | 252 |
| gat ttc att gct aca tat cag gcc aat tat ggc ttc tct aac gat ggc<br>Asp Phe Ile Ala Thr Tyr Gln Ala Asn Tyr Gly Phe Ser Asn Asp Gly<br>                      70                        75                        80 | 300 |
| gca tct agt tct acc gca aat gtt gaa gat gtc cat gct agg act gca<br>Ala Ser Ser Ser Thr Ala Asn Val Glu Asp Val His Ala Arg Thr Ala<br>              85                        90                        95 | 348 |
| gag gaa cct cca caa gaa aaa gcc ccg gaa ccc act gat gcc aga aag<br>Glu Glu Pro Pro Gln Glu Lys Ala Pro Glu Pro Thr Asp Ala Arg Lys<br>            100                      105                      110 | 396 |
| aag gga gaa aaa aga aag gct gag tca gga tgg ttt cat gtt gaa gaa<br>Lys Gly Glu Lys Arg Lys Ala Glu Ser Gly Trp Phe His Val Glu Glu<br>115                        120                      125 | 444 |
| gac aga aat aca aat gta tac gtg tct ggt ttg cct cca gat att aca<br>Asp Arg Asn Thr Asn Val Tyr Val Ser Gly Leu Pro Pro Asp Ile Thr<br>130                        135                      140                      145 | 492 |
| gtg gat gaa ttt ata caa ctt atg tcc aag ttt ggc att att atg aga<br>Val Asp Glu Phe Ile Gln Leu Met Ser Lys Phe Gly Ile Ile Met Arg<br>              150                      155                      160 | 540 |
| gat cct cag aca gaa gaa ttt aag gtc aaa ctt tac aaa gat aat caa<br>Asp Pro Gln Thr Glu Glu Phe Lys Val Lys Leu Tyr Lys Asp Asn Gln<br>            165                      170                      175 | 588 |
| gga aat ctt aaa gga gac ggt ctt tgc tgt tat ttg aaa aga gaa tct<br>Gly Asn Leu Lys Gly Asp Gly Leu Cys Cys Tyr Leu Lys Arg Glu Ser<br>        180                      185                      190 | 636 |
| gtg gaa ctt gca tta aaa ctt ttg gat gaa gat gaa att aga ggc tac<br>Val Glu Leu Ala Leu Lys Leu Leu Asp Glu Asp Glu Ile Arg Gly Tyr<br>195                        200                      205 | 684 |
| aaa tta cat gtt gag gtg gca aag ttt caa ctg aag gga gaa tat gat<br>Lys Leu His Val Glu Val Ala Lys Phe Gln Leu Lys Gly Glu Tyr Asp<br>210                        215                      220                      225 | 732 |
| gcc tca aag aag aag aag aag tgc aaa gac tat aag aag aag ctg tct<br>Ala Ser Lys Lys Lys Lys Lys Cys Lys Asp Tyr Lys Lys Lys Leu Ser<br>              230                      235                      240 | 780 |
| atg caa caa aag cag ttg gat tgg aga cct gag agg cga gcc gga cca<br>Met Gln Gln Lys Gln Leu Asp Trp Arg Pro Glu Arg Arg Ala Gly Pro<br>            245                      250                      255 | 828 |
| tcc cgg atg cgc cat gag cga gtt gtc atc atc aag aat atg ttt cat<br>Ser Arg Met Arg His Glu Arg Val Val Ile Ile Lys Asn Met Phe His<br>260                        265                      270 | 876 |
| cct atg gat ttt gag gat gat ccg ttg gtg ctg aat gag atc aga gaa<br>Pro Met Asp Phe Glu Asp Asp Pro Leu Val Leu Asn Glu Ile Arg Glu<br>275                        280                      285 | 924 |
| gac ctt cga gta gag tgt tcg aag ttt gga caa att agg aaa ctc ctt<br>Asp Leu Arg Val Glu Cys Ser Lys Phe Gly Gln Ile Arg Lys Leu Leu<br>290                        295                      300                      305 | 972 |
| ctc ttt gat agg cac cca gat ggt gtg gcc tct gtg tcc ttt cgg gat<br>Leu Phe Asp Arg His Pro Asp Gly Val Ala Ser Val Ser Phe Arg Asp<br>              310                      315                      320 | 1020 |
| cca gag gaa gct gat tat tgt att cag act ctc gat gga aga tgg ttt<br>Pro Glu Glu Ala Asp Tyr Cys Ile Gln Thr Leu Asp Gly Arg Trp Phe<br>            325                      330                      335 | 1068 |
| ggt ggc cgt caa atc act gcc cag gca tgg gat ggg act aca gat tat<br>Gly Gly Arg Gln Ile Thr Ala Gln Ala Trp Asp Gly Thr Thr Asp Tyr<br>            340                      345                      350 | 1116 |
| cag gtg gag gaa acc tca aga gaa agg gag gaa agg ctg aga gga tgg<br>Gln Val Glu Glu Thr Ser Arg Glu Arg Glu Glu Arg Leu Arg Gly Trp | 1164 |

-continued

```
        355                 360                 365
gag gct ttc ctc aat gct cct gag gcc aac aga ggc ctt agc gtt cag    1212
Glu Ala Phe Leu Asn Ala Pro Glu Ala Asn Arg Gly Leu Ser Val Gln
370                 375                 380                 385 att ctg tct ctg ctt cga aag gca ggg cct tct aga gca agg cat ttt    1260
Ile Leu Ser Leu Leu Arg Lys Ala Gly Pro Ser Arg Ala Arg His Phe
                390                 395                 400 tca gag cac ccc agc aca tct aaa atg aat gct caa gaa act gca act    1308
Ser Glu His Pro Ser Thr Ser Lys Met Asn Ala Gln Glu Thr Ala Thr
            405                 410                 415 gga atg gca ttt gaa gaa cct ata gat gag aag aag ttt gaa aag aca    1356
Gly Met Ala Phe Glu Glu Pro Ile Asp Glu Lys Lys Phe Glu Lys Thr
        420                 425                 430 gaa gat ggg gga gaa ttt gaa gaa ggt gct tct gaa aac aat gct aag    1404
Glu Asp Gly Gly Glu Phe Glu Glu Gly Ala Ser Glu Asn Asn Ala Lys
435                 440                 445 gaa agt agc ccc gaa aaa gag gct gaa gaa ggc tgc cct gaa aaa gaa    1452
Glu Ser Ser Pro Glu Lys Glu Ala Glu Glu Gly Cys Pro Glu Lys Glu
450                 455                 460                 465 tct gaa gag ggc tgc ccc aaa aga ggg ttt gaa ggc agc tgc tcc caa    1500
Ser Glu Glu Gly Cys Pro Lys Arg Gly Phe Glu Gly Ser Cys Ser Gln
                470                 475                 480 aaa gag tct gaa gaa ggc aat ccc gta aga gga tct gaa gag gat agt    1548
Lys Glu Ser Glu Glu Gly Asn Pro Val Arg Gly Ser Glu Glu Asp Ser
            485                 490                 495 cct aaa aaa gag tct aaa aag aag aca ctc aaa aat gat tgt gaa gag    1596
Pro Lys Lys Glu Ser Lys Lys Lys Thr Leu Lys Asn Asp Cys Glu Glu
        500                 505                 510 aat ggc ctt gca aag gaa tct gaa gat gac ctc aac aag gag tct gaa    1644
Asn Gly Leu Ala Lys Glu Ser Glu Asp Asp Leu Asn Lys Glu Ser Glu
515                 520                 525 gag gag gtt ggc ccc aca aaa gag tcc gaa gaa gat gac tca gag aaa    1692
Glu Glu Val Gly Pro Thr Lys Glu Ser Glu Glu Asp Asp Ser Glu Lys
530                 535                 540                 545 gag tct gat gaa gac tgc tct gaa aaa cag tct gaa gat ggc tcc gaa    1740
Glu Ser Asp Glu Asp Cys Ser Glu Lys Gln Ser Glu Asp Gly Ser Glu
                550                 555                 560 aga gaa ttt gaa gaa aat ggt ctc gag aaa gat ttg gac gag gaa ggt    1788
Arg Glu Phe Glu Glu Asn Gly Leu Glu Lys Asp Leu Asp Glu Glu Gly
            565                 570                 575 tct gaa aag gag ctt cat gaa aat gtt ctt gac aaa gag tta gaa gaa    1836
Ser Glu Lys Glu Leu His Glu Asn Val Leu Asp Lys Glu Leu Glu Glu
        580                 585                 590 aat gac tct gaa aac tcc gaa ttt gaa gat gac ggc tct gaa aaa gtg    1884
Asn Asp Ser Glu Asn Ser Glu Phe Glu Asp Asp Gly Ser Glu Lys Val
595                 600                 605 tta gat gag gaa ggc tct gag aga gag ttt gac gaa gat tca gat gaa    1932
Leu Asp Glu Glu Gly Ser Glu Arg Glu Phe Asp Glu Asp Ser Asp Glu
610                 615                 620                 625 aag gaa gaa gag gag gat aca tat gaa aaa gta ttt gat gat gag tct    1980
Lys Glu Glu Glu Glu Asp Thr Tyr Glu Lys Val Phe Asp Asp Glu Ser
                630                 635                 640 gat gag aaa gag gat gaa gaa tat gca gat gaa aag ggg ctt gaa gct    2028
Asp Glu Lys Glu Asp Glu Glu Tyr Ala Asp Glu Lys Gly Leu Glu Ala
            645                 650                 655 gct gat aaa aag gcg gaa gaa ggt gat gca gat gaa aag ctg ttt gaa    2076
Ala Asp Lys Lys Ala Glu Glu Gly Asp Ala Asp Glu Lys Leu Phe Glu
        660                 665                 670 gag tca gat gac aag gaa gat gaa gat gca gat gga aag gaa gtt gaa    2124
```

-continued

```
Glu Ser Asp Asp Lys Glu Asp Glu Asp Ala Asp Gly Lys Glu Val Glu
    675                 680             685 gat gct gac gaa aag ttg ttc gaa gat gat gat tcc aat gag aag ttg         2172
Asp Ala Asp Glu Lys Leu Phe Glu Asp Asp Asp Ser Asn Glu Lys Leu
690                 695                 700                 705 ttt gat gag gag gaa gat tcc agt gag aag ttg ttt gac gat tct gat         2220
Phe Asp Glu Glu Glu Asp Ser Ser Glu Lys Leu Phe Asp Asp Ser Asp
                710                 715                 720 gag agg ggg act ttg ggt ggt ttt ggg agt gtt gaa gaa ggg ccc cta         2268
Glu Arg Gly Thr Leu Gly Gly Phe Gly Ser Val Glu Glu Gly Pro Leu
                725                 730                 735 tcc act ggc agc agc ttt att ctc agt agc gat gat gat gac gat gat         2316
Ser Thr Gly Ser Ser Phe Ile Leu Ser Ser Asp Asp Asp Asp Asp Asp
            740                 745                 750 att taatcccta aacttgcttt ttagggagag tcctccatct acatttgcct gtgctt        2375
Ile cagggtaatt actagtagtg ttacatgaac atgtgcatag tggtaggatg ccatcagatt       2435
aaagcattga agtgtttcat tgttacctgt acctaatggt tttaaatata tgttaattga       2495
ttgtttagtt aaaatgtcat agttacaatg caagtaaact ggatacttgt tcttttgtca       2555
gatttgttaa atgcatgcag aataatattt ttaagagtat tgattgaagt ttgtgatatt       2615
catcaataaa aatgagttga taatatgcag aaactgaaaa aaaaaaaaaa aaaaaaa         2672
```